United States Patent
Adam

(10) Patent No.: US 11,512,281 B1
(45) Date of Patent: Nov. 29, 2022

(54) SUSTAINABLE CONVENTIONAL AND ORGANIC AGRICULTURE WITH REDUCED N AND P FERTILIZER USE

(71) Applicant: Nadia Adam, Mishawaka, IN (US)

(72) Inventor: Nadia Adam, Mishawaka, IN (US)

(73) Assignee: Biomineral Systems LLC, South Bend, IN (US)

( * ) Notice: Subject to any disclaimer, the term of this patent is extended or adjusted under 35 U.S.C. 154(b) by 0 days.

(21) Appl. No.: 17/068,637

(22) Filed: Oct. 12, 2020

Related U.S. Application Data

(63) Continuation of application No. 14/578,494, filed on Dec. 22, 2014, now Pat. No. 10,836,993, and a continuation of application No. 14/578,489, filed on Dec. 22, 2014, now Pat. No. 10,851,027.

(51) Int. Cl.
| | |
|---|---|
| *C12N 1/20* | (2006.01) |
| *A01N 63/20* | (2020.01) |
| *C12N 15/82* | (2006.01) |
| *A01H 3/00* | (2006.01) |
| *C12R 1/01* | (2006.01) |
| *C12R 1/19* | (2006.01) |

(52) U.S. Cl.
CPC .............. *C12N 1/20* (2013.01); *A01H 3/00* (2013.01); *A01N 63/20* (2020.01); *C12N 1/205* (2021.05); *C12N 15/8261* (2013.01); *C12R 2001/01* (2021.05); *C12R 2001/19* (2021.05); *Y02P 60/21* (2015.11)

(58) Field of Classification Search
None
See application file for complete search history.

(56) References Cited

U.S. PATENT DOCUMENTS

| | | | | |
|---|---|---|---|---|
| 5,061,490 A | * | 10/1991 | Paau | ..................... C12N 1/00 424/93.47 |
| 9,364,005 B2 | * | 6/2016 | Mitter | ............... G01N 33/0098 |
| 10,836,993 B2 | * | 11/2020 | Adam | ..................... A01H 3/00 |
| 10,851,027 B2 | * | 12/2020 | Adam | ..................... C12N 1/205 |
| 11,097,991 B1 | * | 8/2021 | Adam | ..................... C05F 11/08 |

OTHER PUBLICATIONS

Sang Hey Ji et al. "Isolation and characterization of plant growth promoting endophytic diazotrophic bacteria from Korean rice cultivars". Microbiological Research 169 (2014), pp. 83-98.*

* cited by examiner

*Primary Examiner* — Vera Afremova

(57) ABSTRACT

Endophytic microbial strains as biocatalysts isolated from fresh plant samples, their compositions, and methods of use thereof to enhance the growth and/or yield of a plant in the presence of reduced (synthetic or otherwise) nitrogen and phosphorus fertilizers are provided. The selected endophytic microbial strains serve as biocatalysts to solubilize organic (proteinaceous) nitrogen otherwise unavailable to plants for their nutritional needs. In addition, selected endophytic microbial strains serve as biocatalysts to solubilize mineral-P and mineralize organic-P otherwise unavailable to plants for their nutritional phosphate needs. Thus defined, biocatalysts will serve to replace or reduce the requirement of (synthetic or otherwise) nitrogen and phosphorus fertilizers. Also provided are materials and methods for inoculating plants with these biocatalysts at carefully selected inoculum densities to reliably reduce the amount of nitrogen and phosphorus fertilizers by 30-50% thus accomplishing optimal yields in a cost-effective manner.

20 Claims, 18 Drawing Sheets

Figure 3

**Table 1. Average Nutrient Analyses (as is)* of Major Types of Manure in Oklahoma**

| Manure Type | Dry Matter % | Total N | $P_2O_5$ | $K_2O$ |
|---|---|---|---|---|
| | | lbs./ton | | |
| Feedlot Manure | 62 | 24 | 21 | 25 |
| Broiler Litter | 77 | 63 | 61 | 50 |
| | | lbs./1000gal | | |
| Lagoon Effluent | 0.5 | 4.2 | 1.0 | 5.0 |
| Lagoon Sludge | 7 | 15 | 16 | 11 |
| Dairy Slurry | 3 | 13 | 11 | 11 |

*$P_2O_5$ and $K_2O$ are commonly used for fertilizer ingredients instead of P and K. Some laboratories may still report in elemental P and K content. To convert, use the following equations: $K_2O = K \times 1.2$ or $P_2O_5 = P \times 2.29$

SUSTAINABLE CONVENTIONAL AND ORGANIC AGRICULTURE WITH REDUCED N AND P FERTILIZER USE

FIELD OF THE INVENTION

The present invention relates to the field of sustainable agriculture. Specifically, the disclosure provides novel purified bacterial populations comprising plant isolated endophytes and synthetic combinations of seeds with heterologously plant derived endophytes to provide a specific benefit that of optimal production of crop plants in the absence of (synthetic or otherwise) nitrogen and phosphate fertilizers or in the presence of (synthetic or otherwise) nitrogen and phosphate fertilizers applied at the rate of 30-50% less than their recommended fertilizer application rates. In particular, the synthetic compositions and methods disclosed herein are useful for enhancing plant growth in the complete absence of (synthetic or otherwise) nitrogen and phosphate fertilizers or in their much reduced presence.

BACKGROUND OF THE INVENTION

The United States is, by far, the largest producer of corn in the world, producing as much as 35% of world's corn, 33% of world's soybean, more than 65% of world's sorghum and is the biggest wheat exporter (Ag 101, US EPA).

Although US currently leads the world in corn production, the portion of agricultural revenue returned to farmers decreased from 37% to 19% from 1950 to 2002 (Atwell et al., 2010). In addition, input costs increased sevenfold and the real price of corn adjusted for inflation decreased fivefold (Duffy, 2006).

One major contributor to the input costs is the cost of fertilizer and pesticides because US farming is fertilizer and pesticide intensive.

The cost of phosphate fertilizer has risen steadily from the year, 2000 doubling in the year 2007 (Olcyzk et al., 2007).

Nitrogen (N) is an essential plant macronutrient; of the three essential macronutrients (N, P, and K), nitrogen is required by plants in the greatest amount and its availability is a major factor limiting growth of plants in natural as well as in agricultural soils (Kraiser et al., 2011). A simplified view of the nitrogen cycle in soils is shown in FIG. 1.

Nitrogen (N) is present in the biosphere in various chemical forms with molecular nitrogen gas ($N_2$) representing 80% of its atmospheric composition (Sanhueza, 1982). Plants however, cannot directly use this form of N. Nitrogen therefore, enters the biological cycle as ammonia/ammonium (either via biological fixation i.e., prokaryotic conversion of $N_2$ to ammonia or production of ammonia by the HaberBosch industrial fixation of $N_2$ as mentioned above) and as atmospheric nitrate (Mannheim et al., 1995). Once N is fixed as nitrate or ammonia, it can have two main fates: (i) nitrate and ammonia can undergo biochemical processes that transform them back to $N_2$ (Mannheim et al., 1995); or they can be reduced and/or assimilated for the biosynthesis of N-containing metabolites such as proteins/peptides. These metabolites (amino acids, urea, small polypeptides) and other N-containing biomolecules can then be released back to the environment by secretion, excretion, or by the decay of organic matter (Jones et al., 2005a).

Historically, the classical paradigm of the terrestrial N cycle has asserted that organic N must be converted into inorganic N ($NO_3$—N, $NH_4$—N) by soil microorganisms prior to becoming available to plant roots, and thus N mineralization (ammonification) has been viewed as the bottleneck in plant N nutrition (Warren and Adams, 2007). Therefore, synthetic N fertilizers applied to support crop growth have always been in the form of ammonium or nitrates.

Previous to the discovery of the Haber Bosch process almost 100 years ago to convert atmospheric $N_2$ to $NH_3$, food production was always limited by the ability to supplement soil nitrogen by crop rotation, leaving the soil fallow or applying manure. However, with cheap production of synthetic N fertilizers, anhydrous ammonia, urea, and urea ammonium nitrate (UAN)—widely used by the US farmers; synthetic N fertilizers have become 'key' to phenomenal increases in crop yields thus promoting agricultural intensification in the US and around the world.

This increase however, has come at a high cost to the environment. For example, Chesapeake bay, the nation's largest estuary is polluted from agricultural operations whose nitrogen (and P) runoff from the synthetic fertilizers applied to the farm fields fills the bay water causing eutrophication, fish kills, and proliferations of human pathogenic bacteria (www.grist.org, 2010*). In the gulf of Mexico which drains the US heartland and the upper Midwest, a deadzone is produced almost the size of 5000-8000 sq. miles in the summer months impacting fisheries along the gulf's borders in Texas, Louisiana, Mississippi, Alabama, and Florida (www.grist.org, 2010*).

The Haber-Bosch process to convert $N_2$ to $NH_3$ requires high temperatures and pressures and is very energy intensive so much so that ~1% of the global energy consumption is required to produce synthetic ammonia for N fertilizer. Therefore, there is a strong correlation between the price of natural gas and oil and fertilizer prices (www.grist.org, 2010*).

The US consumes nearly 12% of the global annual synthetic N fertilizer mostly from declining natural gas reserves and is going to be increasingly dependent on imports from foreign nations such as Trinidad and Tobago, Canada, Russia and Ukraine for its synthetic N fertilizer needs (www.grist.com, 2010*).

Currently, US is able to produce only 45% of its nitrogen fertilizer needs and is tightly consolidated by only 3 to 4 companies namely, CF industries, Terra, and Agrium that are also amongst the nation's largest environmental polluters (www.grist.org, 2010*).

\* http://www.grist.org/article/series/the-n2-dilemma-is-america-fertilizing-disaster Of the applied N fertilizer, only 30-50% is actually taken up by plants. Recent research has shown that this overapplication of synthetic N fertilizer although a quick fix for supplying plant needs also causes overgrowth of bacteria and fungi. According to one line of research, overgrowth of microorganisms in turn could potentially oxidize soil organic carbon critical to maintaining soil quality and the ability to retain soil N thus possibly priming the soils to need progressively more and more of the 'same quick fix' to maintain consistent crop yields (Mulvaney et al., 2006; Mulvaney et al., 2007; Khan et al., 2007; Mulvaney et al., 2009; Mulvaney et al., 2010a; Mulvaney et al., 2010b).

The over-application of N fertilizer also has significant adverse human health effects through leaching of nitrates in the ground water causing methemoglobinemia in infants and reacting with other chemicals in the body to produce N-nitroso compounds that have been linked to birth defects and cancer via model animal studies.

From the economic perspective, although the US currently leads the world in corn production, the portion of agricultural revenue returned to farmers decreased from 37% to 19% from 1950 to 2002 (Atwell et al., 2010). In addition, input costs increased sevenfold and the real price of corn adjusted for inflation decreased fivefold (Duffy, 2006).

Phosphorus fertilizer manufactured from phosphorus rock is mined in the US (Florida), China, Morocco, and Russia. In year 2006 alone, 142 million tons was mined worldwide (Olcyzk et al., 2007), yet, at the current world-wide rate of application of fertilizers, the readily available sources of high grade phosphate rocks will be depleted within the next 60 to 90 years (Runge-Metzger, 1995).

The situation is critical because the supply of phosphate rock in Florida may be exhausted as early as year 2040 according to the Institute of Phosphate Research (Olcyzk et al., 2007).

Phosphate fertilizers have been critical to crop growth because phosphorus deficiency often limits plant growth (Schachtman, et al., 1998; Vance, et al., 2003; Raghothama, and Karthikeyan, 2005) although this essential plant macronutrient is critically important for improving soil fertility in both tropical and temperate regions (Von Uexküll & Mutert, 1995).

The practice of applying chemical (inorganic) P fertilizers to alleviate P deficiency is inefficient for both logistical and economic reasons however, because 75-90% of soluble P from fertilizers rapidly becomes immobilized as Fe—, Al—, or Ca—$PO_4$ phases in soils (Gyaneshwar et al., 2002).

Thus effective means for utilizing residual accumulated insoluble P in soils and a means for increasing efficiency of applied synthetic P fertilizers are critically needed.

This takes on particular significance when we note that global food production needs to increase by 50% in the next 20 years to sustain the increasing world population and prosperity.

Although theoretical estimates have suggested that the accumulated P in agricultural soils is sufficient to sustain maximum crop yields worldwide for about 100 years (Gyaneshwar et al., 2002), most soils are deficient in bioavailable P.

Therefore, sustainable alternatives to improving P bioavailability are needed for maintaining U.S.'s edge in crop production and agricultural productivity in general.

All the above unequivocally show that corn production in particular and crop production in general is unsustainable from all perspectives, including environmental, soil quality, economic, and human health. Hence, invention for a sustainable, cost effective, and similarly reliable alternative to (synthetic or otherwise) N or P fertilizers is critical to maintaining intensive agriculture, global food security, and mitigating the effects of global climate change.

The premise of applying synthetic N fertilizer as $NH_4^+$ and nitrate was based on the conventional wisdom that plants can take up nitrogen in only these forms. However, recent research has shown that in addition to taking up these inorganic forms of nitrogen, uptake of organic nitrogen in the form of oligopeptides and free amino acids is also a major uptake pathway in plants (Jones et al., 2005a; Jones et al., 2005b; Adamcyzk et al., 2009; Kraiser et al., 2011).

Although, historically, the classical paradigm of the terrestrial N cycle has asserted that organic N must be converted into inorganic N ($NO_3$—N, —$NH_4$—N) by soil microorganisms prior to becoming available to plant roots, with N mineralization (ammonification) as the bottleneck in plant N nutrition (Warren and Adams, 2007) soil N is dominated by organic forms and approximately 40% of total soil N is present in the form of polymers such as proteins and peptides (Schulten and Schnitzer, 1997).

Recent research has shown that plants can indeed take up organic nitrogen when liberated from soil polymers such as amino acids bound in peptides and proteins (Jones et al., 2005a; Jones et al., 2005b; Adamcyzk et al., 2009; Kraiser et al., 2011). Several amino acid transporters have been identified in plants such as lysine-histidine transporter 1 (LHT1), amino acid permease 1 (AAP1), and amino acid permease 5 (AAP5) in the roots of *Arabidopsis thaliana* (Hirner et al., 2006; Lee et al., 2007; Svennerstam et al., 2008).

Plants can access N in soil proteins using proteases in root exudates (Paungfoo-Lonhienne et al., 2008). In addition, bacteria colonizing plant roots and known to have a beneficial effect on plant growth (referred to as PGPB aside from the bacteria that fix atmospheric $N_2$) also exude extracellular enzymes such as phosphatases and proteases for respectively, P and N nutritional needs of plants (Kraiser et al., 2011; Ahearn et al., 1968; Gupta et al., 2002).

The de-polymerization of these compounds by enzymes such as proteases creates short peptides and free amino acids (Jamtgard et al., 2010). These free amino acid (FAA) reserves in soils are mostly higher than ammonium and nitrate and offer the largest and most reliable source of FAAs (Lipson and Näsholm, 2001). The bound amino acids (BAAs) for example those in proteins and peptides in soils were significantly higher than mineral-N in unfertilized soil solutions as shown in FIG. 2 except lettuce grown in farm land which had been fertilized with synthetic N fertilizers (Jamtgard et al., 2010).

Indeed field studies have shown evidence for direct uptake of amino acids by plants in diverse ecosystems such as Alaskan tussock tundra, boreal coniferous forest, heathland, subtropical rainforest, and agricultural land further underlining the importance of organic protein-N for plant nutrition (Kielland, 1994; Näsholm et al., 1998; Stribley and Read, 1980; Schmidt and Stewart, 1999; Jones and Darrah, 1994; Yamagata and Ae, 1996; Näsholm et al., 2001; Sauheitl et al., 2001). Direct uptake of N was also shown recently by Tida et al., (2009) in tomato seedlings using $^{15}NH_4Cl$, $K^{15}NO_3$, 1, 2-$^{13}C_2$ $^{15}N$-glycine labeling techniques. They found that the $^{13}C$ and $^{15}N$ increased significantly in tomato seedlings within 48 h after injection into the soil us indicating that organic protein N-uptake by plants is very rapid (Tida et al., 2009), Furthermore, Jones et al., (2005a) addressed the question of competition for amino acids between plants and microorganisms. Although molecules such as amino acids are excellent C and N sources for microbes, they can potentially out compete plant roots for free amino acids (Owen and Jones, 2001), and microbial capture of free amino acids (glycine in this case) is very rapid over a ride range of concentrations (0.1 µM-10 mM) interestingly enough plant uptake of N was maximized at high amino acid concentrations where the microbial utilization was slowest (Jones et al., 2005a).

These results indicate that protein-N can be utilized by plants rapidly in a major way for their nutritional needs in the presence of microorganisms competing for the same source of N (Jones et al., 2005a).

Endophytic bacteria colonize inner host tissues, sometimes in high numbers, without damaging the host or eliciting strong defense responses (Hurek, 2011). Prominent sites for active ingress into roots are the emergence points of lateral roots and to some extent the zone of differentiation and elongation near the root tip, where slightly disrupted or not completely differentiated tissues may facilitate penetration. Intercellular spaces in the epidermal and cortical regions and lysed plant cells are major sites of colonization, with locally high cell densities of up to $(10)^{10}$ cells/cm$^3$ (Chi et al., 2005).

Proteases are a type of extracellular depolymerases; they are released by microorganisms via three known mechanisms; i) substrate induction, ii) end-product repression or de-repression due to insufficient nutrient supply and iii) constitutive production of small amounts (Geisseler et al., 2010). Protease enzymes catalyze amide hydrolysis breaking the peptide bond and releasing individual amino acids via a proton transfer reaction (Karaman, 2011). They can therefore hydrolyze large proteins into peptides and amino acids with wide substrate specificities and can degrade most non-structural proteins (Geisseler et al., 2010).

Production of extracellular proteases is induced by the presence of substrate i.e., proteins in the medium while the presence of easily metabolizable C end products may repress enzyme production (Kalisz, 1988; Haab et al., 1990; Allison and Macfarlane, 1992). Given the abundant presence of protein organic N in soils and applied animal based manures, the microbial propensity to exude proteases, and the ability of plants to take up peptides and free amino acids we hypothesize the following pathway to supply plants N needs (see FIG. 4).

Although bacteria can colonize plants both epiphytically i.e., plant rhizosphere and endophytically in the plant apolplasts, selected endophytic bacteria because they live within the plant and can therefore recover more easily from stressful situations (Kozyrovska et al., 1996). In addition, being away from the natural biocenosis gives them a significant edge in competing with the native soil bacteria (Kozyrovska et al., 1996).

Although both bacteria and fungi produce proteases, we selected bacteria because they generally outnumber their fungal counterparts by 2-150 fold (Hilda and Fraga, 1999). In our quest for selecting the suitable organic (protein) nitrogen solubilizing bacteria we screened endophytic bacteria isolated from natural plant samples and screened them for protease production.

The proposed embodiment will address the current need for sustainable and cost efficient P management in soils by developing a biocatalyst that makes mineral soil-P, and organic-P available for plant needs thus reducing or eliminating the need for the application of synthetic P fertilizers by a combination of utilization of already available soil-P and by increasing the efficiency of applied synthetic-P fertilizer.

The proposed embodiment will have the additional benefit of improving surface and ground water quality because application of manures and fertilizers has resulted in increased transfer of soil P (solid associated) to solution and eventually, via erosion and runoff, to surface waters where it plays a key role in eutrophication and impairment of affected waters as a resource for drinking, recreation and industry.

The total soil P content typically varies between 500 and 2000 mg kg$^{-1}$ (Vance et al., 2003).

Of this, typically 30-50% of the total insoluble P is present as organic P ($P_o$) mainly as inositol phosphate and the remaining is found as Fe-, Al- or Ca-associated mineral phosphate ($P_i$); phosphate dissolved in soil solution ranges between only 0.1 and 10 µM (Bielski, 1973; Ozanne, 1980; Raghothama, 1999; Frossard et al., 2000).

Because plants can only take up phosphorus as dissolved $H_xPO_4^{y-}$ ions, and for optimal crop growth 0.5-0.7 mM dissolved P is needed in the soil solution, most soils are P deficient and crop growth is often limited by P bioavailability.

Application of chemical fertilizers i.e., phosphate salts is used to supplement the limited pools of dissolved P; however, because of high affinity of P binding to Fe-oxyhydroxide, Al-oxyhydoxide minerals and precipitation as calcium-phosphate phases, dissolved P is quickly converted to insoluble P.

The main goal of the preferred embodiment then is to increase the efficacy of chemical fertilizers and to use the already existing substantial reserves of insoluble soil-P, thereby reducing the application of chemical fertilizers.

Toward this goal, we enhance dominant natural mechanisms of insoluble soil-P bioavailability.

Two main mechanisms of making Pi and Po bioavailable for plant's nutritional needs involves secretion of organic acids to solubilize Pi and secretion of phosphatase enzymes for mineralization of Po. These organic acids and phosphatase enzymes are secreted both by soil microorganisms (bacteria and fungi) and to a smaller extent by plant roots in response to P deficiency (Raghothama and Karthikeyan, 2005; Martinez, 1967).

Although both bacteria, and fungi are ubiquitous in soils, $P_i$ solubilizing and $P_o$ mineralizing bacteria (phosphobacteria) generally outnumber their fungal counterparts by 2-150 fold (Hilda and Fraga, 1999); the P solubilization potential of phosphobacteria can therefore be enhanced to serve as an effective biocatalyst in making insoluble 'fixed' P plant available in an eco-friendly, reliable and sustainable manner.

Phosphobacteria have both epiphytic and endophytic modes of association with the host plant (corn, soybean, wheat, and sorghum, and other crops by extension) and the mode of association can affect the efficacy of phosphobacteria.

Colonizing the plant root epiphytically is difficult because the inoculant has to compete with the native soil bacteria (Kozyrovska et al., 1996).

Phosphobacteria with endophytic relationship with host plant reside within apoplastic spaces inside the host plant thus keeping them away from the natural biocenosis giving them a significant edge in competing with the soil bacteria (Kozyrovska et al., 1996; Sturz et al., 2000).

Because, endophytes live within the plant, they can recover more easily from stress situation; they may also form beneficial host-endophyte allelopathies thus protecting the plant from superinfection by soil bacteria (Kozyrovska et al., 1996; Sturz et al., 2000).

SUMMARY OF THE INVENTION

The proposed embodiment pertains to the development of biofertilizer consisting of protease producing endophytic bacteria (BioCat-N) inoculated crop seeds as an environmentally sustainable, and cost-effective alternative to synthetic N fertilizers and as a means of increasing the efficacy of synthetic fertilizers.

The proposed embodiment pertains to the development of biofertilizer consisting of endophytic phosphobacteria (BioCat-P) inoculated crop seeds as an environmentally sustainable, and cost-effective alternative to synthetic fertilizers and/or applied in combination with the synthetic-P fertilizers and BioCat-N as a means of increasing the efficacy of synthetic fertilizers. The present invention relates to the field of sustainable agriculture. Specifically, the disclosure provides microbial compositions and methods useful for the optimal production of crop plants in the absence of synthetic phosphate fertilizers or in the presence of synthetic phosphate fertilizers applied at the rate of 30-50% less than needed. In particular, the compositions and methods disclosed herein are useful for enhancing plant growth in the complete absence of synthetic fertilizers or in their reduced presence.

DETAILED DESCRIPTION OF PREFERRED EMBODIMENTS

Animal manure is rich in valuable macro and micro nutrients and also supplies organic matter to improve the soil's physical and chemical properties and is used in exclusion to synthetic fertilizers in organic farming.

Nitrogen in manure mainly occurs in three forms-organic, ammonia/ammonium, and nitrate of which organic N is the predominant form of N in manure (http://www.poultrywaste.okstate.edu/files/f-2228web.pdf). Similar to organic nitrogen in soils, organic nitrogen in manure also retains the potential to be depolymerized into free amino acids and oligopeptides.

Although the nutrient content of animal manure varies based on method of collection and storage, and animal species, an average nutrient content of manure is summarized in Table 1.

The object of the purported invention is to develop a biocatalyst (BioCat-N) consisting of organic N solubilizing endophytic bacteria that colonize the root and shoot of plants at sufficient inoculum density so as to facilitate adequate dissolution of organic N into oligopeptides and free amino acids that can be taken up readily by plants.

The purported invention will work by inoculating crop seeds with endophytic bacteria primed to release protease an enzyme that depolymerizes proteins and peptides to free amino acids and oligopeptides. A particular advantage of endophytic bacteria is that they do not need to compete with native soil bacteria; they should therefore be able to degrade and depolymerize the proteinaceous organic nitrogen in soils and in soil amendments (e.g., manure) in the vicinity of plant roots thus releasing free amino acids and oligopeptides for the N nutritional needs of the plant. Hence, in part, the present invention describes preparations of novel plant-derived endophytes, and the creation of synthetic combinations of seeds with heterologous plant-derived endophytes as well as the recognition that such synthetic combinations display a specific beneficial property of reducing the nitrogen fertilizer requirement of the agricultural plants newly, created by the present inventors.

BioCat-N is thus purported to increase organic nitrogen availability and uptake by crops be it in fertilized or unfertilized soils.

At Biomineral Systems, we have conducted experiments with corn and sorghum and show evidence of plant growth on poultry manure alone in the complete absence of ammonium and nitrate that exceeded growth of plants growth with $NH_4^+$ and nitrate similar to synthetic fertilizers. Because of the novelty of this discovery, to the best of the inventor's knowledge no products exist that has been scientifically designed to effectively, efficiently and reliably harness this poultry manure a rich source of organic N for plant uptake and supplying the plant's nutritional needs.

Endophytic organic nitrogen solubilizing bacterial selection and evaluation as potential organic nitrogen solubilizing biocatalyst for two crops corn and sorghum is complete.

The preferred embodiment has been evaluated in crop systems in hydroponic, simulated soil systems, and real soils.

The preferred embodiment has included isolation of protease producing endophytic bacteria from plant samples of corn, sorghum, and sugarcane.

Further, the preferred embodiment has involved determining inoculation efficacy of the isolated endophytic bacteria by determining inoculum density in root and shoot of corn and sorghum.

Further, the preferred embodiment has involved using nitrogen deficiency symptoms, root/shoot ratio, and chlorophyll content measurements and demonstrating that corn and sorghum seeds inoculated with selected N solubilizing endophytic bacteria grown with insoluble organic-N species present in soils such as poultry manure performed as well or better than non-inoculated control seeds grown with full strength Hoagland solution containing dissolved inorganic nitrogen.

As part of our invention, we isolated and purified a number of endophytic bacteria from corn, sorghum and sugarcane plant parts. All the isolated and purified bacterial strains were screened quantitatively for their ability to function as endophytic phosphobacteria. This was accomplished by screening for production of organic acids for solubilizing inorganic/mineral phosphorus; and for the production of acid and alkaline phosphatase enzymes for conversion of organic phosphorus to inorganic phosphorus. In addition, phosphobacteria were tested for heterologous inoculation of corn and sorghum seeds.

We were able to purify 12 bacterial strains of endophytic phosphobacteria from corn, sorghum, and sugarcane plants of which only one strain T6 showed production of all three extracellular enzymes for phosphorus solubilization that include organic acids, acid phosphatase, and alkaline phosphatase enzymes. This strain has been deposited as BMS-201 with the NRRL and has the accession number B-67827.

The preferred embodiment comprising synthetic combination of the purified bacterial strain T6 (BMS-201, NRRL accession number B-67827) when tested for its heterologous inoculation of corn and sorghum seeds showed excellent inoculation ability without harming the plant. The preferred embodiment comprising synthetic combination of the purified bacterial strain T6 (BMS-201, NRRL accession number B-67827) heterologously inoculated corn and sorghum seeds were evaluated in crop systems in hydroponic, simulated soil systems, and real soils.

The preferred embodiment has included isolation of Pi solubilizing and acid- and alkaline-phosphatase producing endophytic bacteria from plant samples of corn, sorghum, and sugarcane.

Further, the preferred embodiment has involved determining inoculation efficacy of the isolated endophytic bacteria by determining inoculum density in root and shoot of corn and root and shoot of sorghum.

Further, the preferred embodiment has involved using phosphate deficiency symptoms, root/shoot ratio, and chlorophyll content measurements in demonstrating that corn and sorghum seeds inoculated with selected Pi solubilizing endophytic bacteria grown with insoluble mineral-P species present in soils such as rock-phosphate and iron-phosphate performed as well or better than non-inoculated control seeds grown with full strength Hoagland solution containing dissolved P.

FIG. 12 shows healthy and better growth with no soluble/dissolved phosphorus fertilizer in T6 (BMS-201, NRRL accession number B-67827) heterologously inoculated corn seed compared to the control plants (reference plants that are uninoculated) grown with recommended amounts of phosphorus fertilizer. Uninoculated phosphorus deficient plants in comparison show very poor growth.

In FIG. 13, the ~40% reduction in root and shoot lengths in the reference plant in the absence of dissolved phosphorus fertilizer (treatment labeled 1) compared to the reference plant grown with recommended amounts of phosphorus fertilizer (treatment labeled 2) are clearly indicative of the need for dissolved phosphorus fertilizer for optimal plant growth. In FIG. 12, the plant grown from heterologously inoculated corn seed grown in complete absence of any soluble phosphorus fertilizer (see treatments labeled 3 and 4) grew as well or better than the reference plant grown from uninoculated seed with recommended amounts of dissolved phosphorus fertilizer.

FIG. 14 further shows that the plants grown from T6 (BMS-201, NRRL accession number B-67827) heterologously inoculated corn seed in the absence of all dissolved phosphorus fertilizer have the best chlorophyll contents when compared to uninoculated reference plant grown with recommended amounts of dissolved phosphorus fertilizer and also surprisingly when compared to T4 heterologously inoculated corn seed in the absence of all dissolved phosphorus fertilizer.

FIG. 15 shows healthy and better growth with no soluble/dissolved phosphorus fertilizer in T6 (NRRL accession number B-67827) heterologously inoculated sorghum seed compared to the control plants (reference plants that are uninoculated) grown with recommended amounts of phosphorus fertilizer. Uninoculated phosphorus deficient plants in comparison show very poor growth.

In FIG. 16, the ~40% reduction in root length and ~70% reduction in shoot lengths in the reference plant in the absence of dissolved phosphorus fertilizer (treatment labeled 1) compared to the reference plant grown with recommended amounts of phosphorus fertilizer (treatment labeled 2) are clearly indicative of the need for dissolved phosphorus fertilizer for optimal plant growth. In FIG. 16, plant grown from heterologously inoculated sorghum seed grown in complete absence of any soluble phosphorus fertilizer (see treatments labeled 3 and 4) grew as well or better than the reference plant grown from uninoculated seed with recommended amounts of dissolved phosphorus fertilizer.

DEFINITIONS

'Soil nitrogen' is defined as the sum total of soil-inorganic and soil-organic nitrogen.

'Soil phosphorus' is defined as the sum total of soil-mineral phosphorus and soil-organic phosphorus.

An 'agricultural plant' can be a monocotyledonous or a dicotyledonous plant typically used in agriculture.

A 'reference plant' is a monocotyledonous or a dicotyledonous plant typically used in agriculture that has not been synthetically inoculated by an 'endophytic bacteria' and serves as a control against which the performance of the 'host agricultural plant' to draw conclusions about the success of the invention.

REFERENCES

Allison, C., and Macfarlane, G. T., 1992. Physiological and nutritional determinants of protease secretion by Clostridium sporogenes: characterization six extracellular proteases. Applied Microbiology & Biochemistry, 37, 152-156.

Adamczyk, B., Godlewski, M., Smolander, A., and Kitunen, V, 2009. Degradation of proteins by enzymes exuded by Allium porrum roots—A potentially important strategy for acquiring organic nitrogen by plants. Plant Physiology and Biochemistry, 47, 919-925.

Ahearn, D. G., Meyers, S. P., Nichols, R. A., 1968. Extracellular proteinases of yeasts and yeast like fungi. Applied Microbiology, 16, 1370-1374.

Atwell R. C., Schulte L. A., Westphal L. M., 2010 How to build multifunctional agricultural landscapes in the US Corn Belt: Add perennials and partnerships, Land Use Policy, 27 1082-1090.

Bieleski, R. L., Phosphate pools, phosphate transport, and phosphate availability, Ann. Rev. Plant Physiol. 24 (1973) 225-252.

Chi F., Shen S. H., Cheng H. P., Jing Y. X., Yanni Y. G., Dazzo F. B., 2005. Ascending migration of endophytic rhizobia, from roots to leaves, inside rice plants and assessment of benefits to rice growth physiology. Applied Environmental Microbiology 2005, 71:7271-7278.

Frossard E., Condron L. M., Oberson A., Sinaj S., and Fardeau J. C., Processes governing phosphorus availability in temperate soils., J. Environ. Qual. 29 (2000), 12-53.

Gupta, R., Beg, Q. K., Khan, S., and Chauhan, B., 2002. An overview on fermentation, downstream processing and properties of microbial alkaline proteases. Applied Microbiology and Biotechnology, 60, 381-395.

Geisseler, D., Horwath, W. R., Joergensen, R. G., and Ludwig, B., 2010. Pathways of Nitrogen Utilization by soil microorganisms—A review. Soil Biology & Biochemistry, 42, 2058-2067.

Gyaneshwar, P., Kumar, G. N., Parekh, L. J., and Poole, P. S., Role of soil microorganisms in improving P nutrition of plants. Plant and Soil 245 (2002) 83-93.

Haab, D., Hagspiel, K., Szakmary, K., Kubicek, C. P., 1990. Formation of the extracellular proteases from Trichoderma reesei QM 9414 involved in cellulose degradation. Journal of Biotechnology, 16, 187-198.

Hilda, R., and Fraga, R., 1999. Phosphate solubilizing bacteria and their role in plant growth promotion. Biotechnology Advances, 17, 319-339.

Hinsinger, P., 2001. Bioavailability of soil inorganic P in the rhizosphere as affected by root-induced chemical changes: a review. Plant and Soil, 237, 173-195.

Hirner, A., Ladwig, F., Stransky, H., Okumoto, S., Keinath, M., Hams, A., Frommer, W. B., and Koch, W., 2006. Arabidiopsis LHT1 is a high affinity transporter for cellular amino acid uptake in both root epidermis and leaf mesophyll. The Plant Cell, 18, 1931-1946.

Hurek, B. R., and Hurek, T., 2011. Current Opinion in Plant Biology, 14:435-443

Jamtgard, S., Nasholm, T., and Kerstin, H-D., 2010. Nitrogen compounds in soil solutions of agricultural land. Soil Biology & Biochemistry, 42, 2325-2330.

Jones, D. L., Shannon, D., Junvee-Fortune, T., and Farrar, J. F., 2005. Plant capture of free amino acids is maximized under high soil amino acid concentrations. Soil Biology & Biochemistry, 37, 179-181.

Jones, D. L., and Darrah, P. R., 1994. Amino-acid influx at the soil-root interface of Zea mays and its implications in the rhizosphere. Plants and Soil, 163, 1-12.

Jones, D. L., Healey, J. R., Willette, V. B., Farrar, J. F., Hodge, A., 2005a. Dissolved organic nitrogen uptake by plants—an important N uptake pathway. Soil Biology & Biochemistry, 37, 413-423.

Jones, D. L., Shannon, D., Junvee-Fortune, T., and Farrar, J. F., 2005b. Plant capture of free amino acids is maximized under high soil amino acid concentrations. Soil Biology & Biochemistry, 37, 179-181.

Kalisz, H. M., 1988. Microbial proteinases. Advances in Biochemical Engineering/Biotechnology, 36, 1-65.

Kielland, K., 1994. Amino-acid-absorption by arctic plants-implications for plants-implications for plant nutrition and nitrogen cycling. Ecology, 75, 2373-2383.

Kraiser, T., Gras, D. E., Gutierrez, A. G., Gonzalez, B., and Gutierrez, R. A., 2011. A holistic view of nitrogen acquisition in plants. Journal of Experimental Botany, 62, 1455-1466.

Khan, S. A., Mulvaney, R. L., Ellsworth, T. R., and Boast, C. W., 2007. The myth of nitrogen fertilization for soil carbon sequestration. Journal of Environmental Quality, 36, 1821-1832.

Karaman, R., 2011. Analyzing Kemp's amide cleavage: A model for amidase enzymes. Computational and Theoretical Chemistry 963, 427-434.

Kozyrovska, N., Kovtunovych, G., and Groosova, E. Kuharchuk, P., and Kordyum, V, 1996. Novel inoculants for an environmentally-friendly crop production. Resources Conservation and Recycling, 18, 79-85.

Lee, Y. H., Foster, J., Chen, J., Voll, L. M., Weber, A. P., Tegeder, M., 2007. AAP1 transports uncharged amino acids into roots of Arabidiopsis. The plant Journal, 50, 305-319.

Lipson, D., and Nasholm, T., 2001. The unexpected versatility of plants: organic nitrogen use and availability in terrestrial ecosystems. Oecologia, 128, 305-316.

Martinez, J. R., Organic phosphorus mineralization and phosphatase activity, Folia Microbiologica, 13 (1967) 161-&

Mannheim, T., Braschkat, J., and Marschner, H., 1995. Reduction of ammonia emissions after application of liquid cattle manure on arable land and grassland: Comparison of wide spread application, application in narrow bands and injection. ZEITSCHRIFT FUR PFLANZENERNAHRUNG UND BODENKUNDE, 158, 535-542.

Mulvaney, R. L., Khan, S. A., and Ellsworth, T. R., 2006. Need for a soil-based approach in managing nitrogen fertilizers for profitable corn production. Soil Science Society of America Journal, 70, 172-182.

Mulvaney, R. L., Khan, S. A., and Ellsworth, T. R., 2007. Response to "Comments on 'Need for a soil-based approach in managing nitrogen fertilizers for profitable corn production' and 'Soil organic nitrogen enrichment following soybean in an Iowa corn-soybean rotation'". Soil Science Society of America Journal, 71, 256-256.

Mulvaney, R. L., Khan, S. A., and Ellsworth, T. R., 2009. Synthetic nitrogen fertilizers deplete soil nitrogen: A global dilemma for sustainable cereal production. Journal of Environmental Quality, 38, 2295-2314.

Mulvaney, R. L., Khan, S. A., and Ellsworth, T. R., 2010a. Comments on "Synthetic Nitrogen Fertilizers Deplete Soil Nitrogen: A Global Dilemma for Sustainable Cereal Production," by RL Mulvaney, R. L., Khan, S. A., and Ellsworth, T. R., 2010b. Reply to Additional Comments on "Synthetic Nitrogen Fertilizers Deplete Soil Nitrogen: A Global Dilemma for Sustainable Cereal Production," by R L Mulvaney, S A Khan, and T R Ellsworth in the Journal of Environmental Quality 2009 38:2295-2314. Journal of Environmental Quality, 39, 1530-1532.

Näsholm, T., Ekblad, A., Nordin, A., Giesler, R., Hogberg, M., Hogberg, P., 1998. Boreal forest plants take up organic nitrogen, Nature, 392, 914-916.

Näsholm, T., Huss-Danell, K., Hogberg, P., 2001. Uptake of glycine by field grown wheat. New Phytologist, 150, 59-63.

Olczyk, T., Yuncong, L., Edward, E., Na-Lampag, S., and Fan, X., 2007. Updates on Fertilizer prices. University of Florida IFAS.

Owen, A. G., Jones, D. L., 2001. Competition for amino acids between wheat roots and rhizosphere microorganisms and the role of amino acids in plant N acquisition. Soil Biol. Biochem. 33, 651-657.

Ozanne P. G., 1980 Phosphate nutrition of plants—general treatise. In The role of phosphorus in agriculture. Eds. F E Khasawneh, E C Sample and E J Kamprath. pp. 559-589. American Society of Agronomy, Crop Science Society of America, Soil Science Society of America, Madison, Wis., USA.

Paungfoo-Lonhienne, C., Lonhienne, T. G., Rentsch, D., Robinson, N., Christies, M., Webb, R. I., Gamage, H. K., Carroll, B. J., Schenk, P. M., Schmidt, S., 2008. Plants can use protein as a nitrogen source without assistance from other organisms. Proceedings of the National Academy of Sciences USA, 105, 4524-4529.

Raghothama K. G., Phosphate acquisition. Ann. Rev. Plant Physiol. Mol. Biol. 50 (1999) 665-693.

Raghothama, K. G. and Karthikeyan, A. S. Phosphate acquisition, Plant Soil 274 (2005) 37-49.

Runge-Metzger, A., 1995, Closing the cycle: Obstacles to efficient P management for improved global food security. In Phosphorus in the Global Environment: Transfers, cycles and Management. Ed. H Tiessen. pp. 27-42. John Wiley and Sons, NY.

Sanhueza, E., 1982. The role of the atmosphere in nitrogen cycling. Plant and Soil, 67, 61-71.

Schulten, H. R., and Schnitzer, M., 1997. The chemistry of soil organic nitrogen: a review. Biology and Fertility of Soils, 26, 1-15.

Svennerstam, H., Ganeteg, U., Näsholm, T., 2008. Root uptake of cationic amino acids by Arabidiopsis depends on functional expression of amino acid permease 5, New Phytologist, 180, 620-630.

Stribley, D. P., Read, D. J., 1980. The biology of mycorrhiza in the Ericaceae. 7. The relationship between mycorrhizal infection and the capacity to utilize simple and complex organic nitrogen-sources. New Phytologist, 86, 365-371.

Schmidt, S., and Stewart, G. R., 1999. Glycine metabolism by plant roots and its occurrence in Australian plant communities. Australian Journal of Plant Physiology, 26, 253-264.

Schachtman, D. P., Reid, R. J., Ayling, S. M., Phosphorus uptake by plants from soil to cell, Plant Physiol. 116 (1998) 447-453.

Sauheitl, L., Glaser, B., and Weigelt, A., 2009. Uptake of intact amino acids by plants depend on soil amino acid concentrations. Environmental and Experimental Botany, 66, 145-152.

Sommerfield, T. G., Chang, C., 1985. Changes in soil properties under annual application of feedlot manure and different tillage practices. Soil Sci. Soc. Am. J. 49, 983-988.

Sturz, A. V, Christie, B. R., Nowak, J., Bacterial endophytes: Potential role in developing sustainable systems of crop production, Critical reviews in plant sciences, 19 (2000) 1-30.

Tida, G. E., Song, S., Roberts, P., Jones, D. L., Huang, D., and Iwasaki, K., 2009. Environmental and Experimental Botany, 66, 357-361.

Vance, C. P., Uhde-Stone, C., Allan, D. L., Phosphorus acquisition and use: critical adaptations by plants for securing a nonrenewable resource, New Phytol. 157 (2003) 423-447.

Von Uexküll H. R., Mutert, E., 1995. Global extent, development and economic-impact of acid soils. Plant and soil 171 (1995) 1-15.

Yamagata, M., and Ae, N., 1996. Nitrogen uptake response of crops to organic nitrogen. Soil Science and Plant Nutrition, 42, 389-394.

Warren, C. R., Adams, P. R., 2007. Uptake of nitrate, ammonium and glycine by plants of Tasmanian wet eucalypt forests. Tree Physiol. 27, 413-419.

http://www.grist.org/article/series/the-n2-dilemma-is-America-fertilizing-disaster Simplified soil nitrogen cycle—http://www.ipm.iastate.edu/ipm/icm/2005/9-19/fiftydegrees.html

BRIEF DESCRIPTION OF DRAWINGS

FIG. 3: Average nitrogen analysis of types of manure

EXAMPLE 1: ISOLATING ENDOPHYTIC BACTERIA FROM FRESH PLANT SAMPLES

Figure 1:
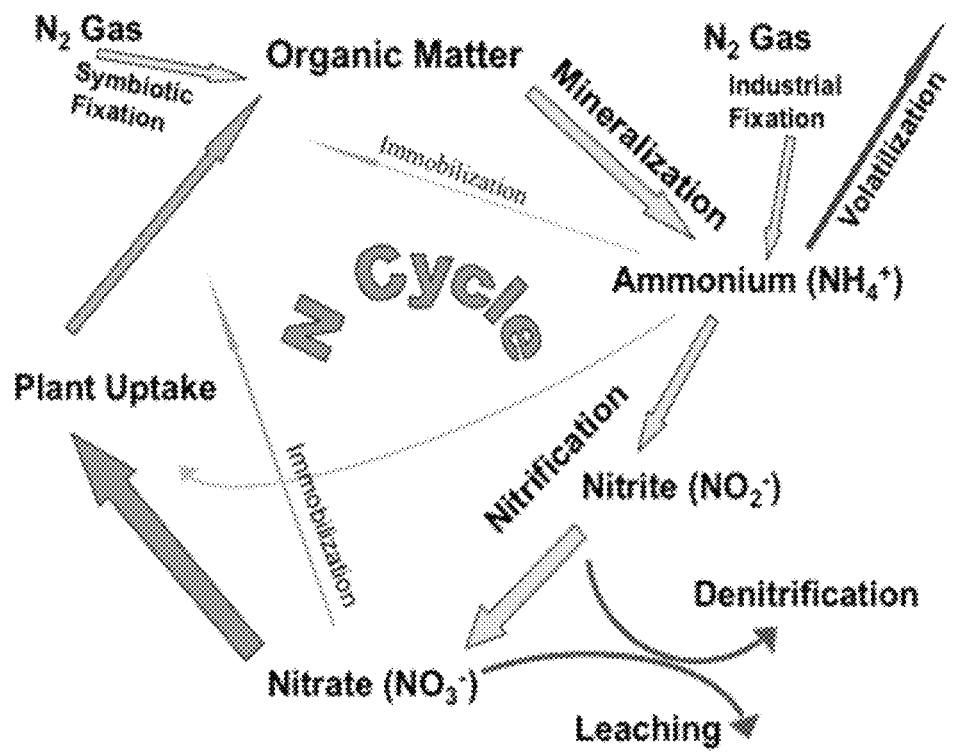
FIG. 1: A simplified view of the nitrogen cycle
Figure 2:
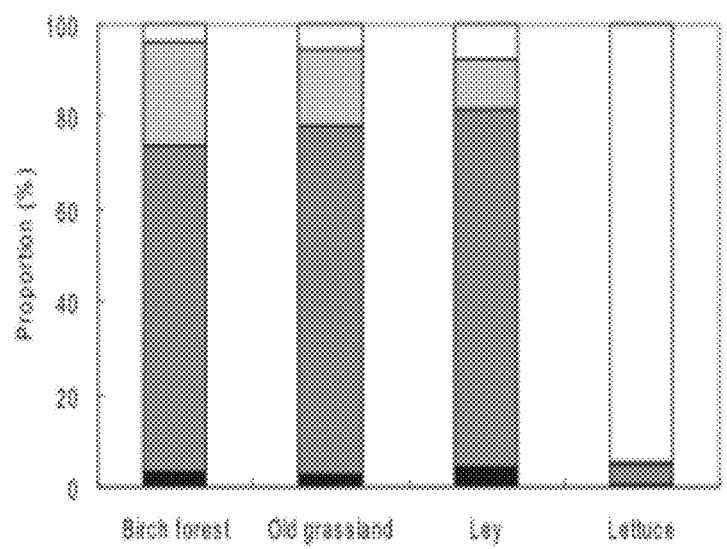
FIG. 2: Proportions of free amino acids (black bars), bound amino acids (dark grey bars), ammonium (light grey bars) and nitrate (white bars) in soil solutions adapted from Jamtgard et al., (2010).
Figure 4:
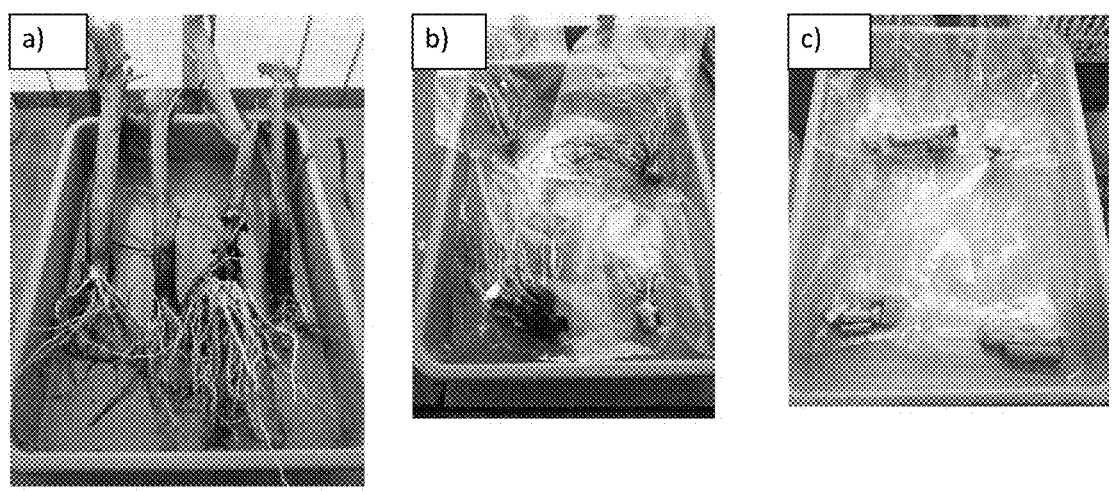
FIG. 4: Endophytic bacteria isolated from plants corn, sorghum, sugarcane: a) corn plants washed in tap water; b) separated roots and shoots; c) separated and chopped corn shoots for further surface sterilization and grinding to isolate endophytic bacteria
Figure 5:
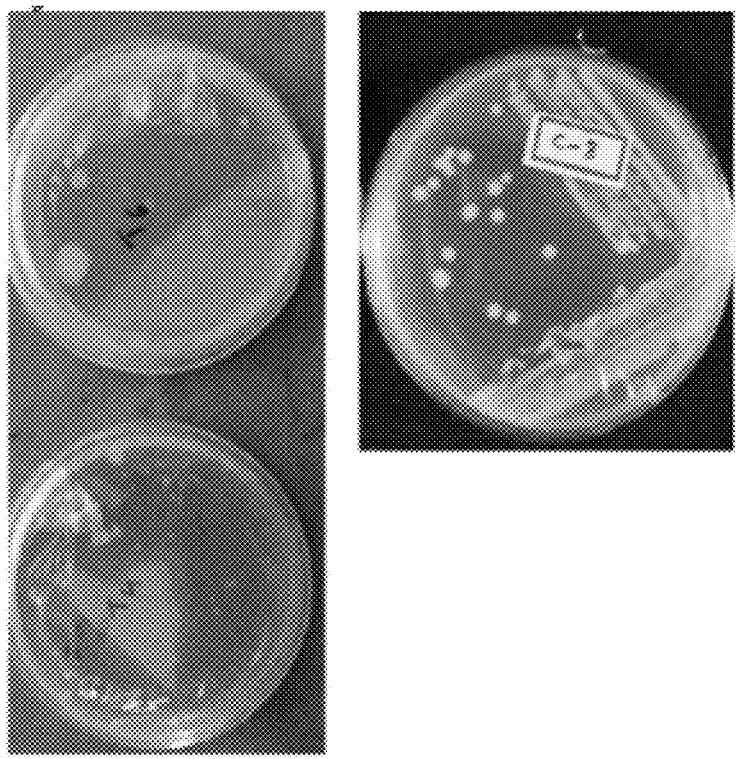
FIG. 5: Endophytic bacteria isolated from corn plants
Figure 6:
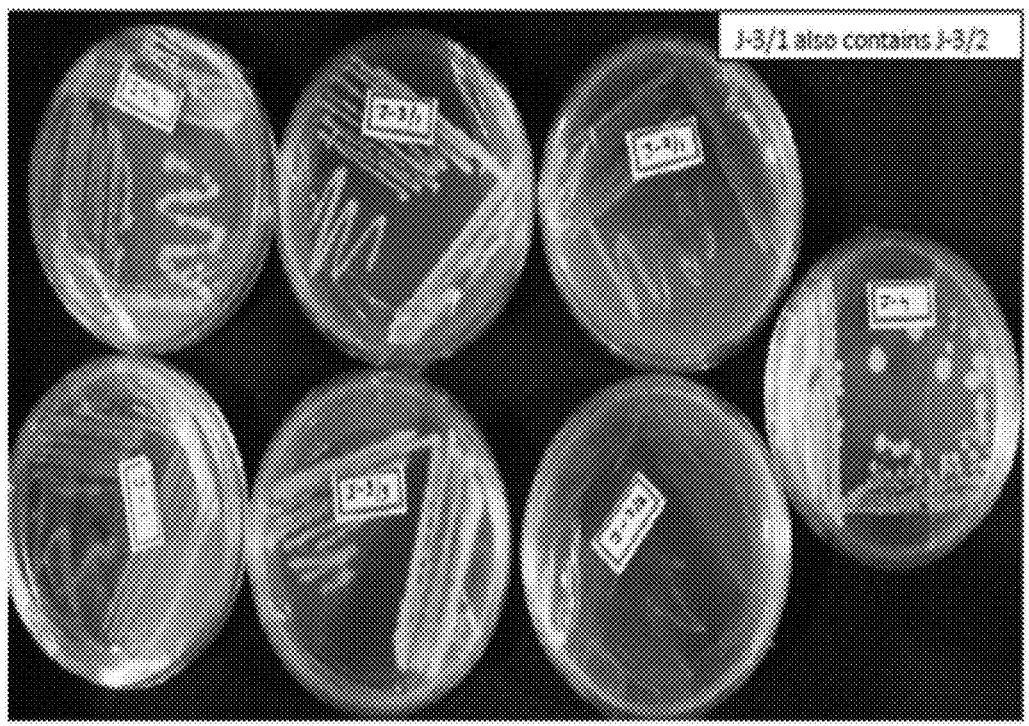
FIG. 6: Endophytic bacteria isolated from sorghum plants
Figure 7:
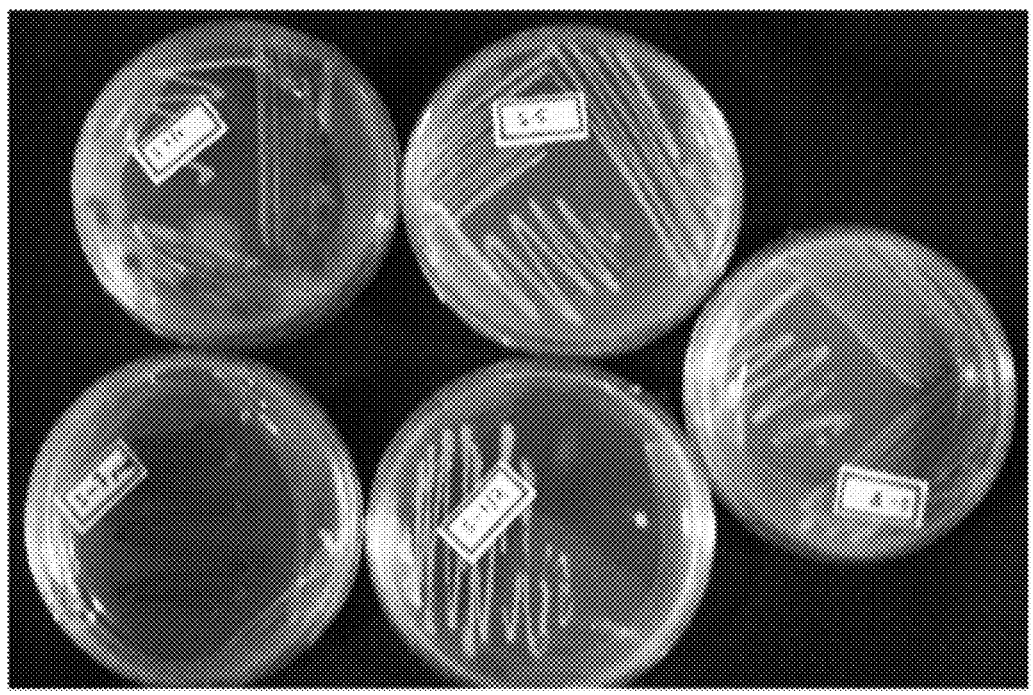
FIG. 7: Endophytic bacteria isolated from sugarcane plants
Figure 8:
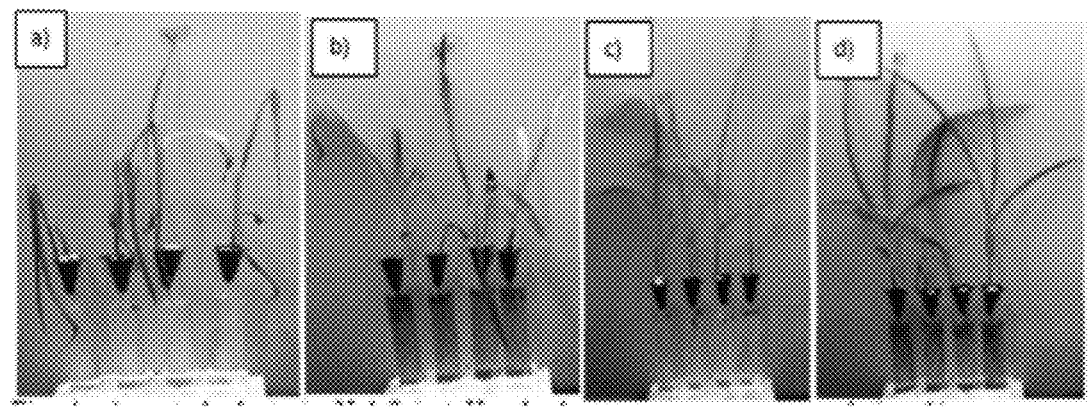
FIG. 8: a) control plants in N-deficient Hoagland solution; b) non-inoculated corn plant grown in complete Hoagland solution amended with 1 g poultry manure; c) non-inoculated corn plants grown in complete Hoagland solution; d) corn plant inoculated with J2/2 grown in N-deficient Hoagland solution amended with 1 g poultry manure.
Figure 9:
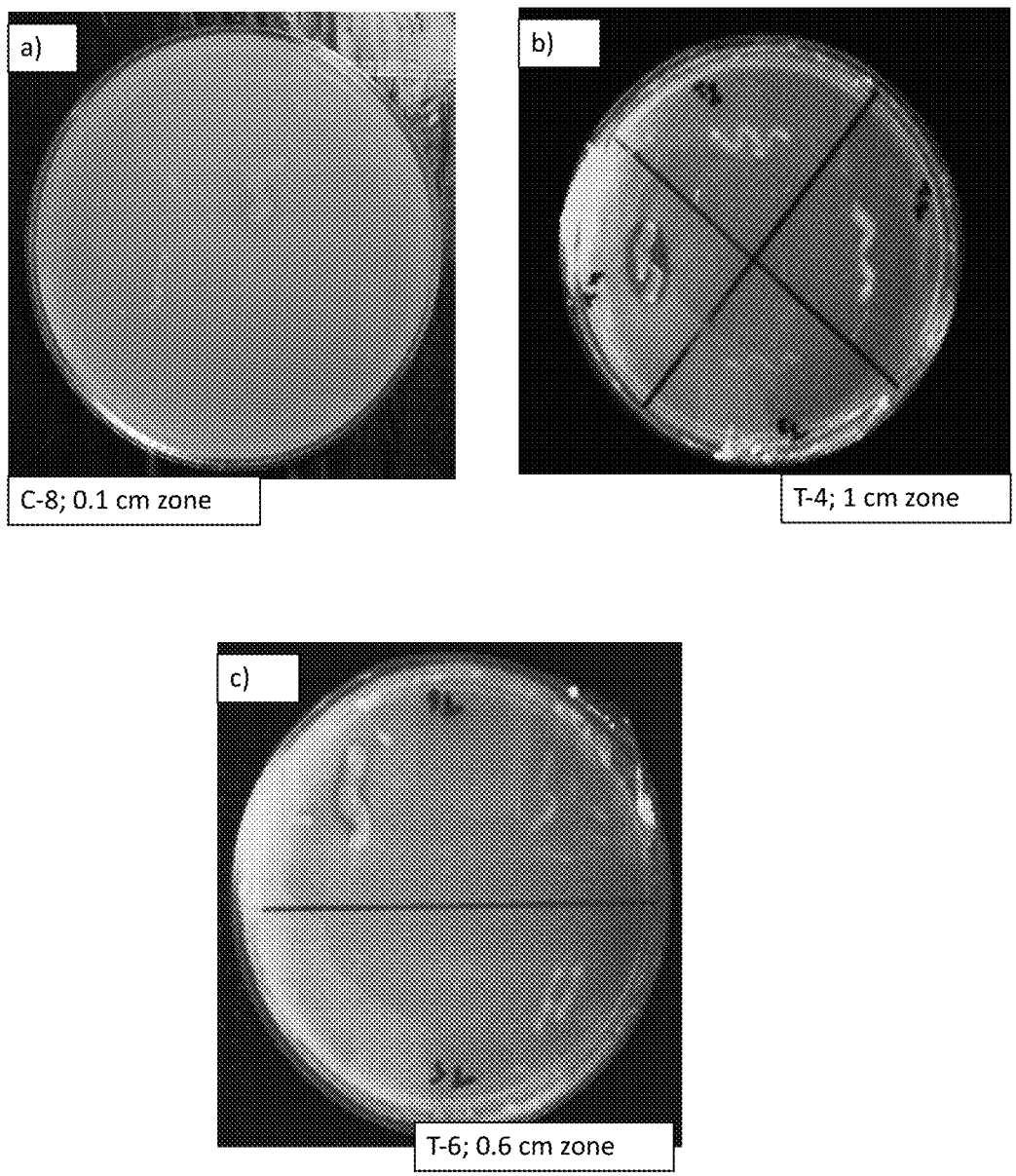
FIG. 9: a), b), and c) showing endophytic bacteria isolated from corn plants that solubilize based on sperber's $PO_4$ solubilizing assay
Figure 10:
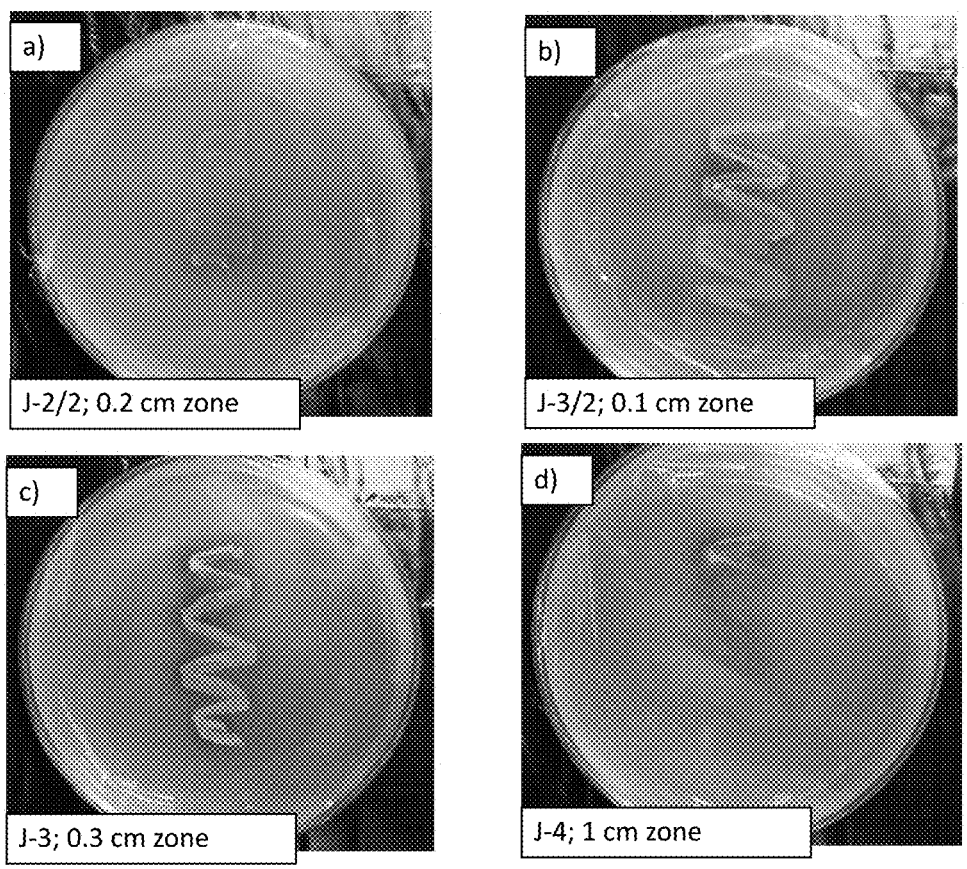
FIG. 10: a), b), c) and d) showing endophytic bacteria isolated from sorghum plants that solubilize based on sperber's $PO_4$ solubilizing assay
Figure 11:
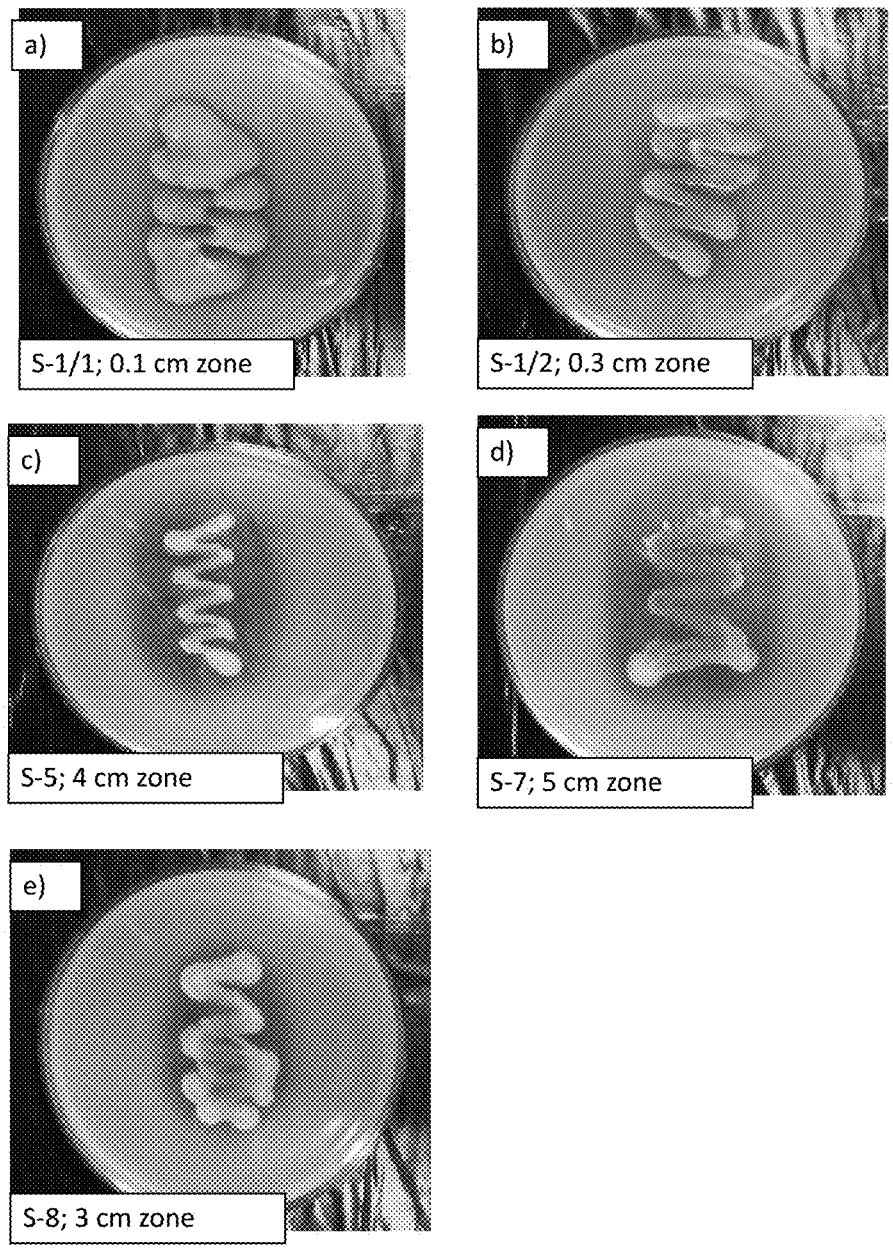
FIG. 11: a), b), c) d) and e) showing endophytic bacteria isolated from sugarcane plants that solubilize $P_i$ based on sperber's $PO_4$ solubilizing assay
Figure 12:
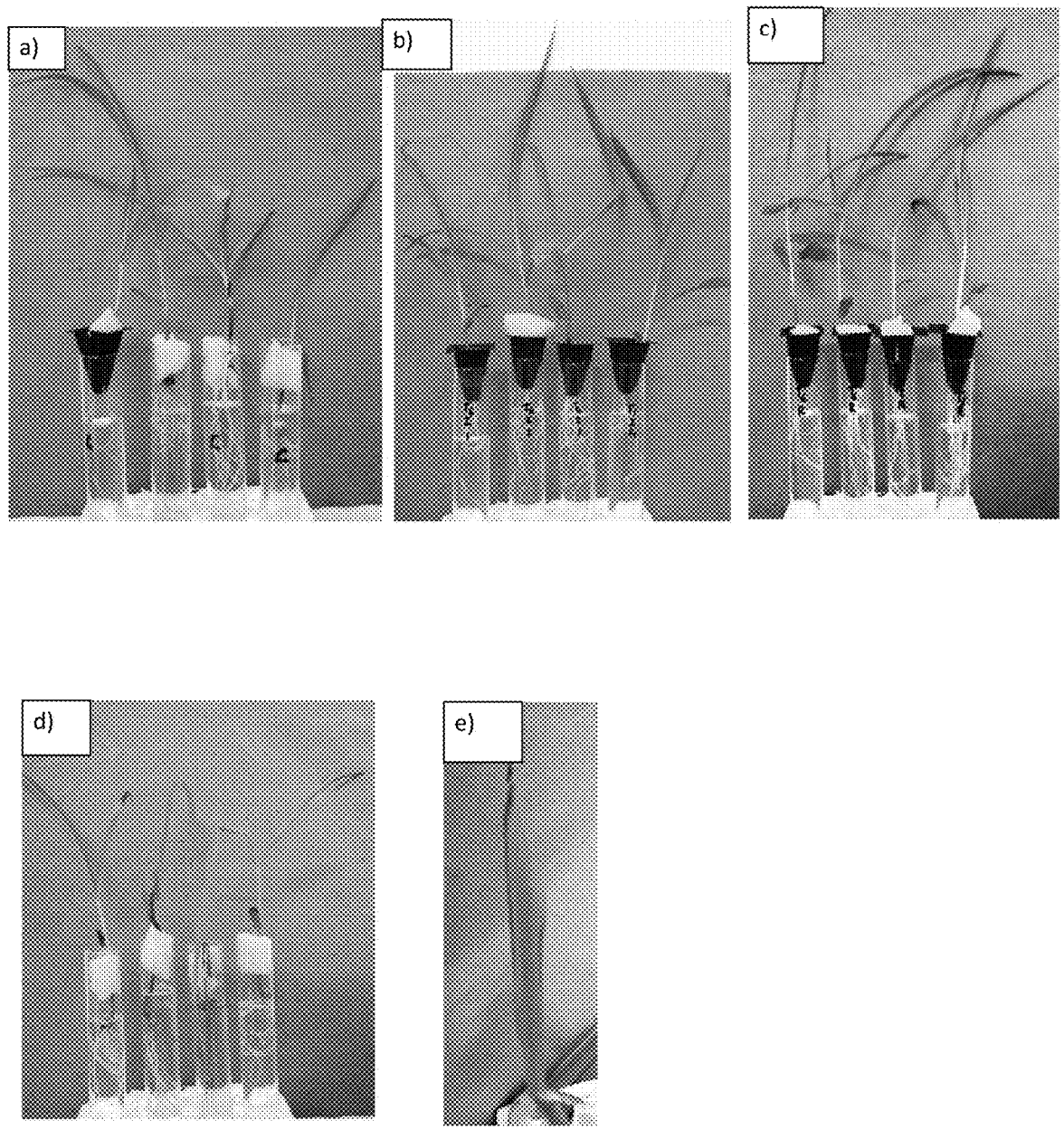
FIG. 12: a) control plants in complete Hoagland solution; b) corn plant inoculated with T6 (BMS-201) grown in modified Hoagland solution amended with 0.2 g rock phosphate; c) corn plant inoculated with T6 (BMS-201) grown in modified Hoagland solution amended with 0.1 g iron-phosphate; d) and e) non-inoculated corn growing in phosphate deficient Hoagland solution
Figure 13:
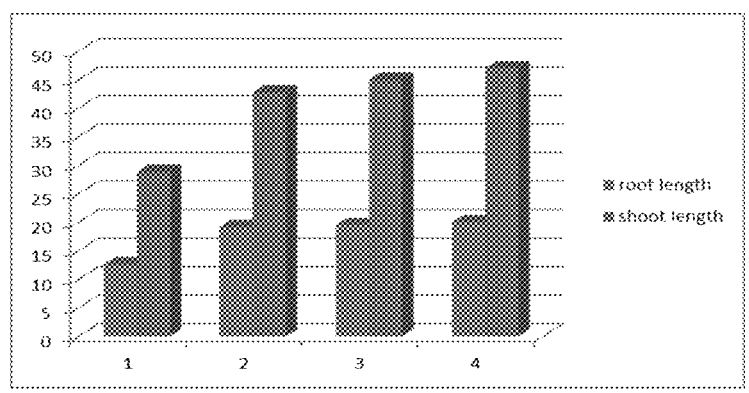
FIG. 13: root and shoot length plotted for 1) control plant grown in phosphate deficient Hoagland solution show very poor growth as measured by their poor root and shoot lengths indicative of yield; 2) corn plant grown in complete Hoagland solution as expected are healthy and show good/optimal root and shoot growth; 3) corn plant grown in phosphate deficient Hoagland solution amended in iron-phosphate nanoparticles show root length and shoot lengths better than the reference/control plants; 4) corn plants grown in phosphate deficient Hoagland solution amended in rock-phosphate also show root length and shoot lengths better than the reference/control plants
Figure 14:
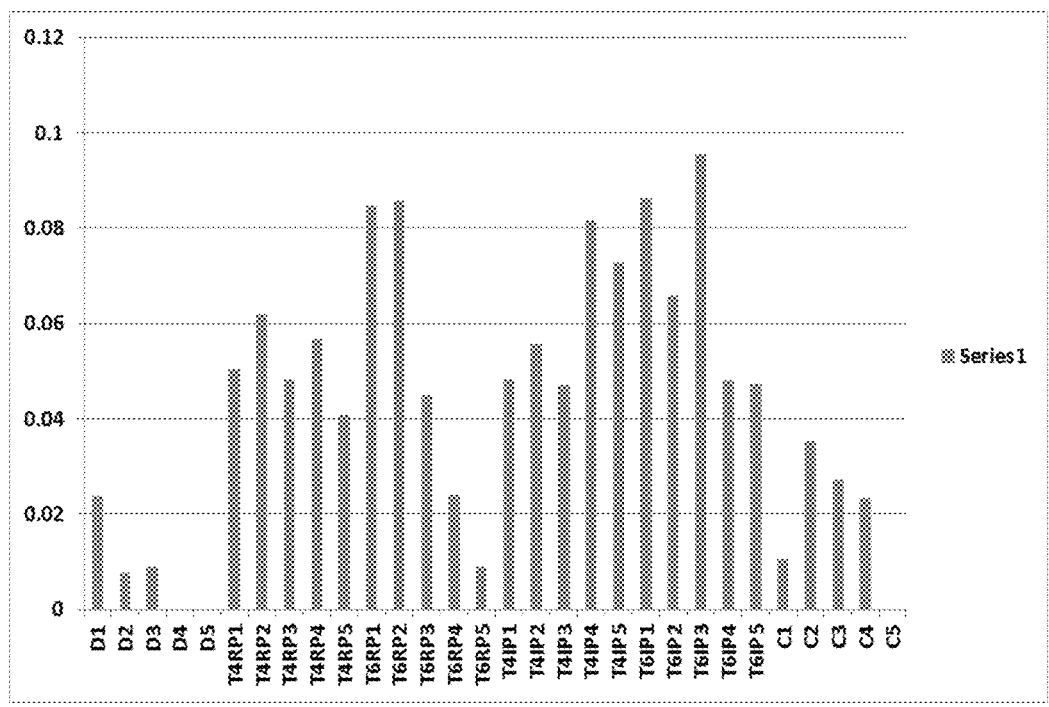
FIG. 14: Total chlorophyll content comparing T6, and T4 inoculated corn grown on rock phosphate (T4RP, T6RP) and iron phosphate, respectively (T4IP, T6IP), and control plants (D) and corn plants grown in full strength Hoagland solution (C)
Figure 15:
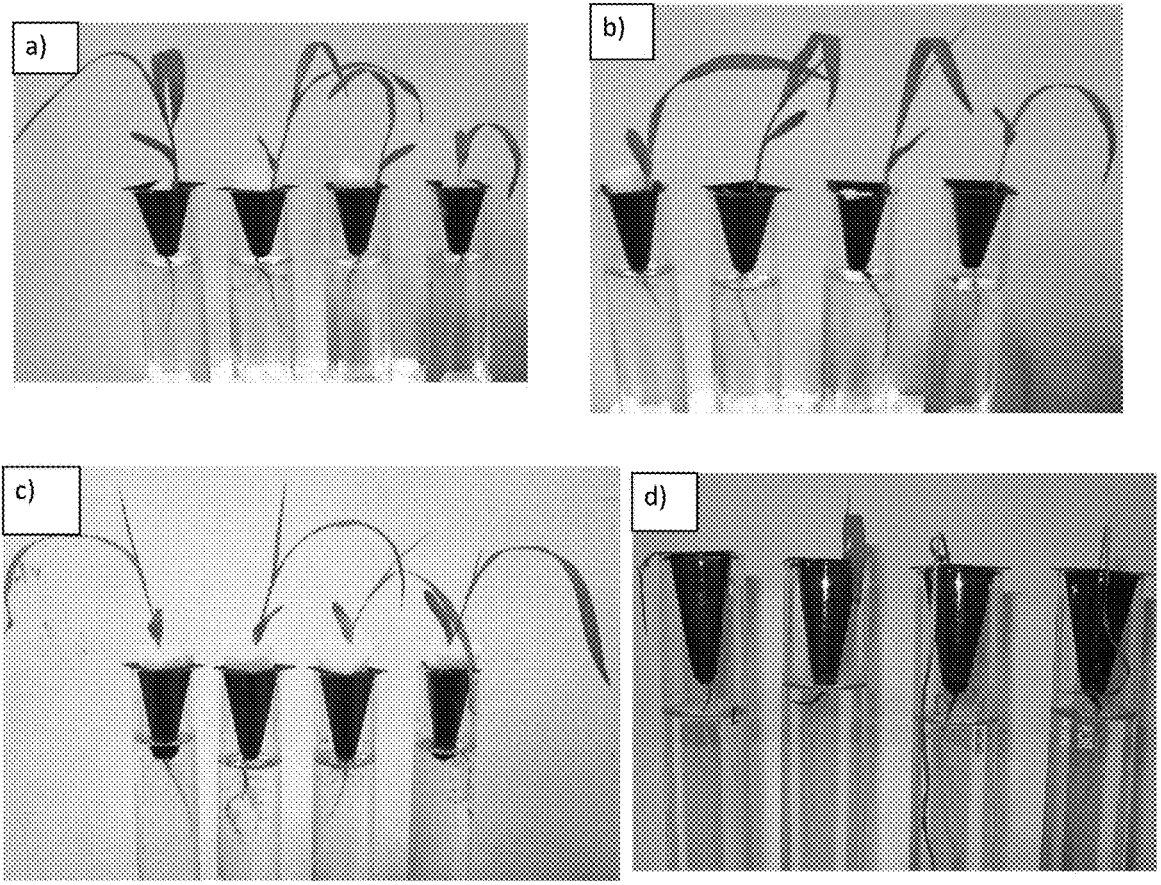
FIG. 15: a) sorghum control plants in complete Hoagland solution; b) sorghum plant inoculated with T6 grown in modified Hoagland solution amended with 0.1 g iron phosphate nanoparticles; c) sorghum plant inoculated with T6 grown in modified Hoagland solution amended with 0.2 g rock-phosphate; d) non-inoculated sorghum growing in phosphate deficient Hoagland solution
Figure 16:
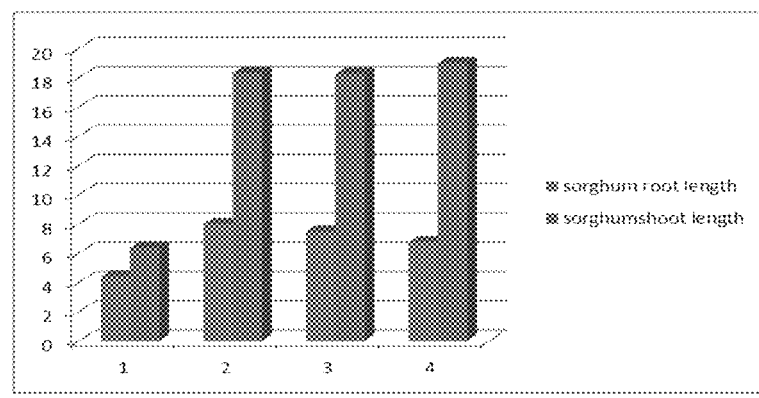
FIG. 16: root and shoot length plotted for 1) control plant grown in phosphate deficient Hoagland solution show very poor growth as measured by their poor root and shoot lengths indicative of yield; 2) sorghum plant grown in complete Hoagland solution as expected are healthy and show good/optimal root and shoot growth; 3) T6 (BMS-201) inoculated sorghum plant grown in phosphate deficient Hoagland solution amended with iron-phosphate nanoparticles show root length and shoot lengths same as reference/control plants; 4) T6 (BMS-201) inoculated sorghum plants grown in phosphate deficient Hoagland solution amended with rock-phosphate show root length and shoot lengths slightly better than the reference/control plants.
Figure 17:
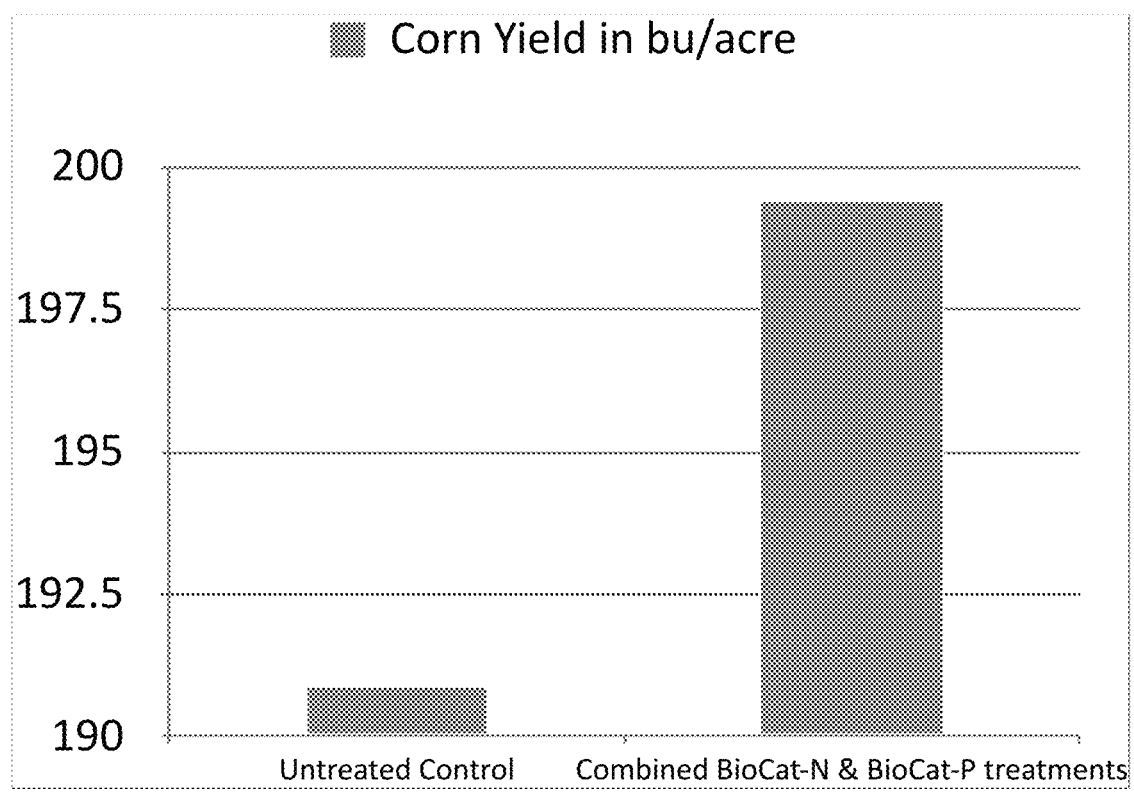
FIG. 17: A comparison of untreated Seed corn yields with combined T6 (BMS-201) and J2/2 (BMS-101) treated seed corn yields with no reduction in fertilizer. Combined T6 (BMS-201) and J2/2 (BMS-101) seed treatment yielded an 8.5 bushel/acre advantage compared to the untreated control.
Figure 18:
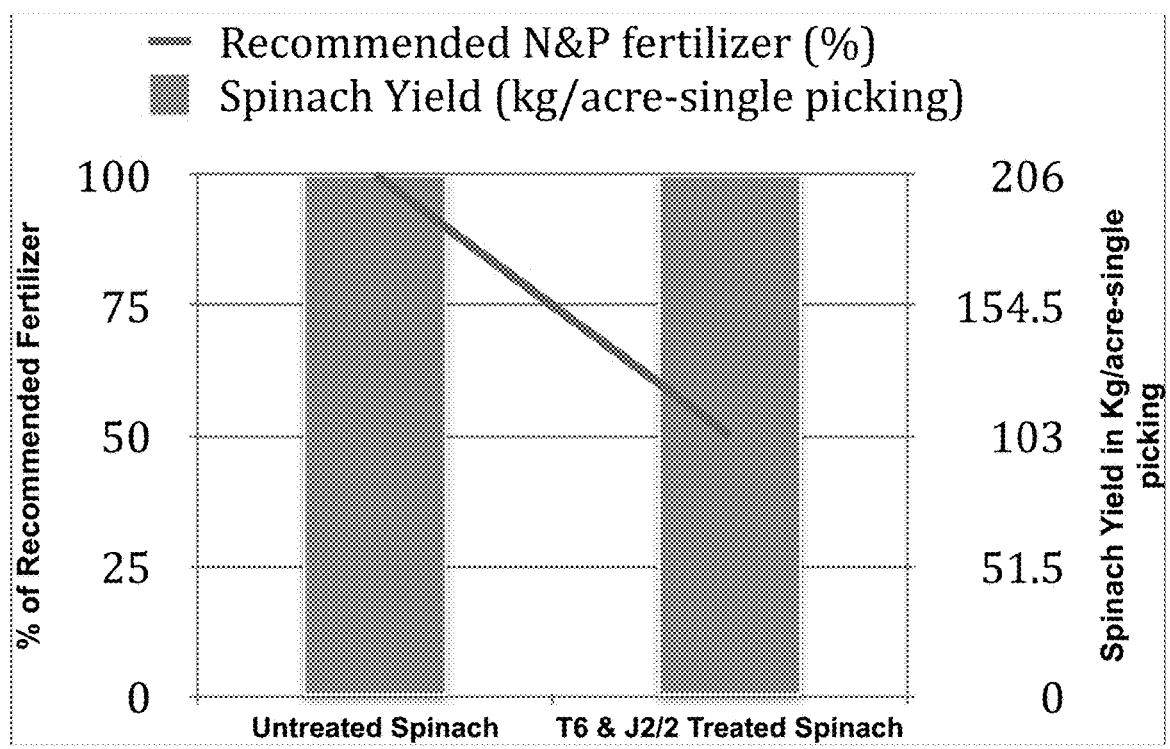
FIG. 18: A comparison of untreated spinach yields at 100% of recommended N and P fertilizers with spinach yields in combined T6 (BMS-201) and J2/2 (BMS-101) treatment with 50% reduction in both N and P fertilizers compared to recommended amount. T6 (BMS-201) and J2/2 (BMS-101) treated spinach showed excellent yields similar to the untreated spinach even with 50% reduction in N& P fertilizer amounts

Fresh samples of corn, sorghum, and sugarcane plants were acquired and washed in tap water. The roots and shoots from each plant was separated. The roots and shoots were separated and chopped. They were then surface sterilized to eliminate any epiphytic bacteria and to facilitate isolation of only endophytic bacteria. The samples were then ground to isolate endophytic bacteria. Endophytic bacteria isolated from corn plants included T4, T6, and C8. Endophytic bacteria isolated from sorghum plants included J-1, J-2/1, J-2/2 (BMS-101, NRRL accession #B-67826), J-3/1, J-3/2, J-3/3, and J-4. Endophytic bacteria isolated from sugarcane plants included S-1/1, S-1/2, S-5, S-7, and S-8.

EXAMPLE 2: CHARACTERIZING ACID AND ALKALINE PROTEASE PRODUCTION FROM THE ISOLATED ENDOPHYTIC BACTERIA

Acid protease assay: Protease activity was determined using the modified Anson method as described in Hashimoto et al., (1973). Briefly, reaction mixture was prepared by combining 1 ml of enzyme solution and 5 ml of bovine casein in 0.05 M acetate buffer (pH 2.5) and incubated at 30 degree C. for 10 minutes. Five ml of 0.11 M trichloroacetic acid was added to stop the reaction. The reaction mixtures was filtered after incubation at 30 degree C. for 30 minutes. Five ml of 0.55 M sodium carbonate was added to 2 ml of the filtrate followed by the addition of 1 ml of thrice diluted phenol reagent. Acid protease activity exuded by endophytic bacteria was quantified based on the concentration of tyrosine measured at 660 nm.

Alkaline protease assay: Alkaline protease activity was determined according to the procedure of Smita et al., (2012). The assay medium (50 ml) containing nutrient broth and 1% casein at pH 10 was inoculated with each isolate and incubated at 37 degree C. for 48 hrs in a water bath shaker. After incubation, the broth cultures were centrifuged at 10,000 rpm for 10 minutes at 4 degree C. and the supernatant was collected to determine the activity of alkaline protease. The activity of alkaline protease was determined similar to the procedure described above for acid protease by measuring the release of tyrosine at 280 nm. The main difference was that the pH was adjusted to pH 10 instead of 2.5 by addition of Glycine-NaOH buffer.

Because Acid-protease are very effective at the common soil pHs we selected J2/2 (BMS-101, NRRL accession #B-67826) an endophytic bacteria isolated from sorghum and tested its inoculation efficacy in corn and sorghum.

TABLE 2

| Endophytic bacteria isolated from corn (C, T), surgarcane (S) and sorghum (J) | Concentration of Tyrosine produced (µg/ml) as an estimation of acid protease activity |
|---|---|
| J3/1 | 159.4 |
| S-7P | 66 |
| J2/2 (BMS-101, NRRL accession # B-67826) | 126 |
| S-1/2 | 55.7 |
| J-4 | 112.6 |
| T-4 | 24.8 |
| T-6 | 18.5 |
| S-8 | 46.4 |
| S-7 | 54 |
| S-5 | 58.4 |
| S-1/12 | 42.8 |
| J2/1 | 102.6 |
| J-3/3 | 52.6 |
| J-1 | 94 |
| C-8 | 44.9 |

TABLE 3

| Endophytic bacteria isolated from corn (C, T), surgarcane (S) and sorghum (J) | Concentration of Tyrosine produced (µg/ml) as an estimation of alkaline protease activity |
|---|---|
| S-1/2 | 77 |
| S-8 | 89 |
| S-7 P | 97 |
| S-1/3 | 87 |

EXAMPLE 3: TESTING INOCULATION EFFICACY OF ENDOPHYTIC BACTERIA

The inoculum for endophytic bacteria was grown under controlled conditions for 48 hrs to inoculum density of $10_8$ to $10_{10}$ cfu/ml. The inoculum was centrifuged and suspended in sterile PBS to a concentration of $10_8$ cfu/ml. The seeds were surface sterilized with 95% ethanol for 2 min and 2.5% sodium hypochlorite for 20-30 min followed by washing seven times in sterile water. Surface sterilized seeds were soaked in sterile PBS containing endophytic bacteria and placed in a temperature controlled incubator shaker at 25 degree C. for exactly 30 minutes. The inoculated seeds were washed with 70% alcohol for 2 minutes and with 2% sodium hypochlorite followed by washing with sterile water 5 times. The surface sterilized seeds were placed in sterile petriplates containing 0.7% of water agar, 5-10 seeds per plate. The seed containing plates were transferred to growth chamber set at 30 degree C. and left for 48 hours to germinate. Well germinated seeds with shoot and roots were separated and surface sterilize with 95% of ethanol for 5 min and 20 min with 4% sodium hypochlorite followed by 4-5 times sterile water rinse. The water rinsed root and shoot parts were transferred to PBS containing solution and ground to rapture the tissue. 1 ml of ground tissue was diluted in 9 ml of sterile water serial dilutions were continued to obtain 100 and 1000 fold dilution and spread on nutrient agar plates. After growth the colonies were counted and tabulated. Non-inoculated seeds served as negative controls.

Based on the amounts of protease production J3/1 and J2/2 (BMS-101, NRRL accession #B-67826) were selected for testing their inoculation efficacy in corn and sorghum. Because J3/1 inoculum density measurements in roots and shoot replicates showed wide variability, J2/2 (BMS-101, NRRL accession #B-67826) was chosen as the protease producing strain for further experiments. The non-inoculated control seeds showed zero inoculum density in the root and shoots.

TABLE 4

Inoculation efficacy of endophytic bacteria in corn and sorghum

| Sample description | cfu/ml (calculated using 1000 fold dilution) |
|---|---|
| J2/2 (BMS-101, NRRL accession # B-67826) inoculum density in corn root | $2.4 \times 10^6$ |
| J2/2 (BMS-101, NRRL accession # B-67826) inoculum density in corn shoot | $3.1 \times 10^5$ |
| J2/2 (BMS-101, NRRL accession # B-67826) inoculum density in sorghum root | $6.6 \times 10^6$ |
| J2/2 (BMS-101, NRRL accession # B-67826) inoculum density in sorghum shoot | $1.8 \times 10^6$ |

Un-inoculated corn and sorghum seeds showed zero inoculum density in roots and shoots

EXAMPLE 4

Standard Hoagland solutions (hydroponic nutrient solutions) were prepared according to the composition in (ref) and contained $Ca(NO_3)_2.4H_2O$, $NH_4NO_3$, KCl, $KNO_3$, $Mg(NO_3)_2.6H_2O$, $KH_2PO_4$, $Fe(NO_3)_3.9H_2O$, Na HEDTA, $MnCl_2.4H_2O$, $H_3BO_3$, $ZnSO_4.7H_2O$, $CuSO_4.5H_2O$, and $Na_2MoO_4.2H_2O$. The young corn seedlings cannot tolerate full strength Hoagland solution. Hence 1/2 strength Hoagland solution was used from VE to V1 vegetative stage. The plants were grown until V3 vegetative growth stage because nitrogen deficiency symptoms can be observed during V1 to V3 growth stage. Nitrogen deficient Hoagland solution was prepared by eliminating all sources of nitrates and ammonium nitrogen and contained $CaCl_2.2H_2O$, KCl, $K_2SO_4$, $MgCl_2.6H_2O$, $KH_2PO_4$, $FeCl_3.6H_2O$, Na HEDTA, $MnCl_2.4H_2O$, $H_3BO_3$, $ZnSO_4.7H_2O$, $CuSO_4.5H_2O$, and $Na_2MoO_4.2H_2O$. Poultry manure was added at the rate of g/L.

The viable inoculated seeds were placed in a muslin cloth and washed with running tap water and dried by placing on autoclaved tissue paper. The seeds were surface sterilized in laminar flow hood with 70% alcohol for 30 minutes and then by washing with 10% sodium hypochlorite solution for 20 minutes. After surface sterilization, the seeds were washed with sterile water, excess water removed by blotting with autoclaved tissue paper, and then air dried under laminar flow. Five to ten surface sterilized and dried seeds were then placed in sterile petriplates containing water soaked blotting paper and transferred to growth chamber maintained at 25-27 degree C. and left for 48 hours to germinate. After seeds germinated, they were transferred to hydroponic reactors. Hydroponic reactors constituted of root permeable plastic buckets. Air pump with air controllers were used to provide aeration to the plants in hydroponic systems and all systems were maintained under greenhouse conditions at a temperature of 24±2 degree C. and relative humidity of 70±3%. After control plants showed nitrogen deficiency symptoms, the plants were removed from hydroponic reactors and washed under running tap water to completely remove Hoagland solution. The plant was dried with blotting paper while taking care to not damage the roots.

Reduced leaf area and degradation of chlorophyll in leaves is symptomatic of nitrogen deficiency so we measured chlorophyll a and chlorophyll b in plants. A single leaf per plant was used for obtaining 10 leaf discs of 1 cm each and weighed. Five of these leaf discs were placed per tube containing 5 ml of 1:1 ratio of DMSO:acetone and the tubes were placed in the dark overnight to allow chlorophyll leaching. After chlorophyll leaching the solution turns green and the concentration of chlorophyll in leaves is calculated by measuring absorbance at 645, and 663 nm. The total chlorophyll is estimated using the following formulae:

Chlorophyll II a (g/l)=0.0127 $A_{663}$–0.00269 $A_{645}$

Chlorophyll II b (g/l)=0.0029 $A_{663}$–0.00468 $A_{645}$

Total Chlorophyll (g/l)=0.0202 $A_{663}$+0.00802 $A_{645}$

EXAMPLE 5: TESTING ENDOPHYTIC BACTERIA FOR INORGANIC-P SOLUBILIZATION

Sperber's media for screening Pi solubilizing endophytic bacteria: The basal Sperber (1958) medium was used and contained glucose 10.0 g/l, yeast extract 0.5 g/l, $CaCl_2$ 0.1 g/l, $MgSO_4.7H_2O$ 0.25 g/l and agar 15.0 g/l. The medium was supplemented with 2.5 g/L of $Ca_3(PO_4)_2$ (TCP-tricalcium phosphate) as P source to appraise the ability of the strains to mobilize inorganic P sources. The pH of the medium was adjusted to 7.2 before autoclaving. The media were distributed in 9 cm diameter Petri plates and marked in four equal parts after solidification. Using the drop plate method, each part was inoculated with innocula. All tests were performed with four replications. Inoculated plates were incubated in dark at 27 degree C. and the diameter of clear zone (halo) surrounding the bacterial growth as well as the diameter of colony were measured after 10, 20 and 30 days.

TABLE 1

Results of Sperber's $PO_4$ solubilizing Assay

| Endophytic bacteria isolated from corn (C, T), surgarcane (S) and sorghum (J) | Phosphate solubilizing activity (zone in cm) |
|---|---|
| C-8 | Very low (0.1 cm) |
| T-4 | Medium (1 cm) |
| T-6 | Medium (0.6 cm) |
| J-2/2 | Very low (0.2 cm) |
| J-3/2 | Very low (0.1 cm) |
| J-3/1 | Very low (0.3 cm) |
| J-4 | Medium (1 cm) |
| S-1/1 | Very low (0.1 cm) |
| S-1/2 | Very low (0.3 cm) |
| S-5 | Very high (4 cm) |
| S-7 | Very high (5 cm) |
| S-8 | High (3 cm) |

EXAMPLE 6: TESTING ENDOPHYTIC BACTERIA FOR ACID PHOSPHATASE PRODUCTION

Screening for acid phosphatase producing endophytic bacteria: The isolated strains were grown in 50 ml of liquid medium (0.1% Ca-phytate; 1.5% glucose; 0.2% $NH_4NO_3$; 0.05% KCl; 0.05% $MgSO_4.7H_2O$; 0.03% $MnSO_4.4H_2O$; 0.03% $FeSO_4.7H_2O$, pH 5.5) in 500-ml flask and incubated at 28 degree C. for 48 hours on reciprocal shaker (200 rpm). The cells were collected from 1 ml of culture by centrifugation at 5000×g for 10 minutes in cool room (40 C) and re-suspended in acetate buffer (0.2 M, pH 5.5). The reaction mixture was prepared. It consisted of 0.8 ml acetate buffer (0.2 M, pH 5.5) containing I mM Na-phytate and 0.2 ml of cell suspension. After incubation for 30 minutes at 37 degree C., the reaction was stopped by adding 1 ml of trichloroacetic acid. One ml aliquot was analyzed for inorganic phosphate liberated using the colorimetric procedure. One unit of enzyme activity was defined as the amount of enzyme liberating 1 n mol of inorganic phosphate per minute.

TABLE 2

Results of acid phosphatase assay

| Endophytic bacteria isolated from corn (C, T), surgarcane (S) and sorghum (J) | Concentration of acid phosphatase produced (mg/l) |
|---|---|
| J-1 | 0.60 |
| S-5 | 0.60 |
| C-8 | 0.58 |
| J-4 | 0.57 |
| S-7 | 0.62 |
| J-2/2 | 0.52 |
| T6 | 0.60 |
| J3/1 | 0.62 |
| T4 | 0.61 |
| S-1/2 | 0.60 |
| J-2/1 | 0.59 |

EXAMPLE 7: TESTING ENDOPHYTIC BACTERIA FOR ALKALINE PHOSPHATASE PRODUCTION

Screening for alkaline phosphatase producing endophytic bacteria: The endophytic bacteria were grown in blood agar for 24 h. One colony was transferred and incubated at 37 degree C. in 2.75 ml of propanediol buffer (0.2 mol/liter, pH 7.5) containing 2 mg of 5-bromo-4-chloro-3-indolyl phosphate previously dissolved in 0.25 ml of N,N-dimethyl formamide. 0.2 ml of $MgCl_2$ (5 mmol/liter) was added as an activator. Alkaline phosphatase production was examined every 30 minutes for 4 h by looking for a blue-green indigo precipitate development on the bacterial growth causing the entire solution to become blue.

TABLE 3

Results of alkaline phosphatase assay

| Endophytic bacteria isolated from corn (C, T), surgarcane (S) and sorghum (J) | Change of color to indigo blue-green |
|---|---|
| C-8 | Negative |
| T-4 | Negative |
| T-6 | Positive |
| J-1 | Negative |
| J-2/1 | Negative |
| J-2/2 | Negative |
| J-3/2 | Negative |
| J-3/1 | Negative |
| J-3/3 | Negative |
| J-4 | Negative |
| S-1/1 | Negative |
| S-1/2 | Negative |
| S-5 | Negative |
| S-7 | Negative |
| S-8 | Negative |

EXAMPLE 8: TESTING INOCULATION EFFICACY OF ENDOPHYTIC BACTERIA

The inoculum for endophytic bacteria was grown under controlled conditions for 48 hrs to inoculum density of $10^8$ to $10^{10}$ cfu/ml. The inoculum was centrifuged and suspended in sterile PBS to a concentration of $10^8$ cfu/ml. The seeds were surface sterilized with 95% ethanol for 2 min and 2.5% sodium hypochlorite for 20-30 min followed by washing seven times in sterile water. Surface sterilized seeds were soaked in sterile PBS containing endophytic bacteria and placed in a temperature controlled incubator shaker at 25 degree C. for exactly 30 minutes. The inoculated seeds were washed with 70% alcohol for 2 minutes and with 2% sodium hypochlorite followed by washing with sterile water 5 times. The surface sterilized seeds were placed in sterile petriplates containing 0.7% of water agar, 5-10 seeds per plate. The seed containing plates were transferred to growth chamber set at 30 degree C. and left for 48 hours to germinate. Well germinated seeds with shoot and roots were separated and surface sterilize with 95% of ethanol for 5 min and 20 min with 4% sodium hypochlorite followed by 4-5 times sterile water rinse. The water rinsed root and shoot parts were transferred to PBS containing solution and ground to rapture the tissue. 1 ml of ground tissue was diluted in 9 ml of sterile water serial dilutions were continued to obtain 100 and 1000 fold dilution and spread on nutrient agar plates. After growth the colonies were counted and tabulated. Non-inoculated seeds served as negative controls.

TABLE 4

Inoculation efficacy of endophytic bacteria in corn and sorghum

| Sample description | cfu/ml (calculated using 1000 fold dilution) |
|---|---|
| Corn-root inoculated with T6 (BMS-201; NRRL accession number B-67827) | $2.1 \times 10^6$ |
| Corn-shoot inoculated with T6 (BMS-201; NRRL accession number B-67827) | $1.7 \times 10^5$ |
| Sorghum-root inoculated with T6 (BMS-201; NRRL accession number B-67827) | $2.6 \times 10^6$ |
| Sorghum-shoot inoculated with T6 (BMS-201; NRRL accession number B-67827) | $3.4 \times 10^5$ |

Un-inoculated corn and sorghum seeds showed zero inoculum density in roots and shoots EXAMPLE 9: TESTING THE EFFICACY OF ENDOPHYTIC INOCULATION FOR ELIMINATING CHEMICAL FERTILIZERS IN CONTROLLED HYDROPONIC SYSTEMS Standard Hoagland solutions (hydroponic nutrient solutions) were prepared and contained $Ca(NO_3)_2.4H_2O$, $NH_4NO_3$, KCl, $KNO_3$, $Mg(NO_3)_2.6H_2O$, $KH_2PO_4$, $Fe(NO_3)_3.9H_2O$, Na HEDTA, $MnCl_2.4H_2O$, $H_3BO_3$, $ZnSO_4.7H_2O$, $CuSO_4.5H_2O$, and $Na_2MoO_4.2H_2O$. The young corn seedlings cannot tolerate full strength Hoagland solution. Hence 1/2 strength Hoagland solution was used from VE to V1 vegetative stage. The plants were grown until V3 vegetative growth stage because phosphate deficiency symptoms can be observed during V1 to V3 growth stage. Phosphate deficient Hoagland solution was prepared by eliminating $KH_2PO_4$.

The viable inoculated seeds were placed in a muslin cloth and washed with running tap water and dried by placing on autoclaved tissue paper. The seeds were surface sterilized in laminar flow hood with 70% alcohol for 30 minutes and then by washing with 10% sodium hypochlorite solution for 20 minutes. After surface sterilization, the seeds were washed with sterile water, excess water removed by blotting with autoclaved tissue paper, and then air dried under laminar flow. Five to ten surface sterilized and dried seeds were then placed in sterile petriplates containing water soaked blotting paper and transferred to growth chamber maintained at 25-27 degree C. and left for 48 hours to germinate. After seeds germinated, they were transferred to hydroponic reactors. Hydroponic systems were maintained under greenhouse conditions at 23-24 degree C., 70% relative humidity, and 12 hours photo-period. Seeds were first grown in full strength Hoagland solution and then transplanted into hydroponic reactors for all the treatments and controls. Five replications were used for all treatments and controls.

Hydroponic reactors constituted of root permeable plastic buckets. Air pump with air controllers were used to provide aeration to the plants in hydroponic systems and all systems were maintained under greenhouse conditions at a temperature of 24±2 degree C. and relative humidity of 70±3%. After control plants showed phosphate deficiency symptoms, the plants were removed from hydroponic reactors and washed under running tap water to completely remove Hoagland solution. The plant was dried with blotting paper while taking care to not damage the roots. The roots were separated from the shoots by using sharp scissors and were weighed to record fresh weight of samples. The root and shoot samples were also dried in the dry air oven at 40 degree C. for 2 days and their dry weight was recorded. The root:shoot ratio of individual plants was calculated and recorded.

Reduced leaf area and degradation of chlorophyll in leaves is also symptomatic of phosphate deficiency so we also measure chlorophyll a and chlorophyll b in plants. A single leaf per plant was used for obtaining 10 leaf discs of 1 cm each and weighed. Five of these leaf discs were placed per tube containing 5 ml of 1:1 ratio of DMSO:acetone and the tubes were placed in the dark overnight to allow chlorophyll leaching. After chlorophyll leaching the solution turns green and the concentration of chlorophyll in leaves is calculated by measuring absorbance at 645, and 663 nm. The total chlorophyll is estimated using the following formulas:

Chlorophyll II a (g/l)=0.0127 $A_{663}$–0.00269 $A_{645}$

Chlorophyll II b (g/l)=0.0029 $A_{663}$–0.00468 $A_{645}$

Total Chlorophyll (g/l)=0.0202 $A_{663}$+0.00802 $A_{645}$

What is claimed is:

1. A novel synthetic combination comprising purified bacterial populations in association with a seed of an agricultural plant, wherein the purified bacterial populations comprise a plant bacterial endophyte that is heterologous to the seed, having all the identifying characteristics of NRRL accession no. B-67826, and is capable of producing protease to solubilize soil organic nitrogen at all relevant agricultural soil pHs, combined with another purified bacterial population comprising a plant bacterial endophyte that is heterologous to the seed having all the identifying characteristics of NRRL B 67827, and capable of producing organic acids, acid phosphatase, and alkaline phosphatase enzymes to solubilize soil phosphorus at acid and alkaline soil pHs and wherein the plant bacterial endophytes of NRRL accession no.'s B-67826 and B 67827 are both present on the surface of a seed or inside the seed and in an amount effective to improve nitrogen and phosphorus fertilizer use efficiency to increase plant's physiological properties for optimal plant growth and yield in organic and conventional agriculture compared to a reference agricultural plant grown under the same conditions in the absence of any purified bacterial endophyte treatments.

2. The synthetic combination of claim 1 which is made by first growing endophytic bacteria having all the identifying characteristics of NRRL B 67826 and NRRL B 67827 each to a specific inoculum density of $10^8$ to $10^{10}$ cfu/ml then suspending in sterile PBS medium to a concentration of $10^8$ cfu/ml, then preparing the seeds by surface sterilizing with 95% ethanol for 2 min and 2.5% sodium hypochlorite for 20-30 min followed by washing seven times in sterile water, then soaking the aforementioned surface sterile seeds in the said endophytic inoculum and henceforth placed in a temperature controlled incubator at 25 degree C. for exactly 30 minutes, then washing the thus prepared inoculated seeds with 70% alcohol for 2 minutes and with 2% sodium hypochlorite followed by washing with sterile water 5 times.

3. The synthetic combination of claim 1 wherein one or more seeds are of corn, sorghum, wheat, rice, and other vegetable, fruit, flower or grass plant and wherein the endophytic bacteria have all the identifying characteristics of NRRL B 67826 and NRRL B 67827 in the said seeds is capable to grow within the tissue of the said plants including its roots or shoots to a concentration of 10^8 to 10^10 cfu/g without reducing germination or yield.

4. The synthetic combination of claim 1, wherein the combination is combined with one or more of an insecticide, fungicide, nematicide, and biostimulant applied either as a seed treatment or as a foliar or soil rhizospheric treatment.

5. The synthetic combination of claim 1 wherein the plant bacterial endophytes are obtainable from a different cultivar, variety or crop as compared to the seed.

6. The synthetic combination of claim 1 wherein the nitrogen fertilizer can be nitrogen fertilizers used in conventional agriculture that are granular, liquid, or powder or a combination of these including but not limited to urea, anhydrous ammonia, urea ammonium nitrate, and ammonium nitrate.

7. The synthetic combination of claim 1 wherein the nitrogen fertilizer can be nitrogen fertilizers used in organic agriculture that are granular, liquid, or powder or a combination of these including but not limited to manure based fertilizers, composted fertilizers, high N– bat guano, and single cell based proteins/.

8. A novel synthetic combination comprising purified bacterial populations in association with a seed of an agricultural plant, wherein the purified bacterial populations comprise a plant bacterial endophyte that is heterologous to the seed, having all the identifying characteristics of NRRL accession no. B-67826, and is capable of producing protease to solubilize soil organic nitrogen at all relevant agricultural soil pHs, combined with another purified bacterial population comprising a plant bacterial endophyte that is heterologous to the seed having all the identifying characteristics of NRRL B 67827, and capable of producing organic acids, acid phosphatase, and alkaline phosphatase enzymes to solubilize soil phosphorus at acid and alkaline soil pHs and wherein the plant bacterial endophytes of NRRL accession no.'s B-67826 and B 67827 are both present on the surface of a seed or inside the seed and in an amount effective to increase yield in organic and conventional agriculture compared to a reference agricultural plant grown under the same conditions with no reduction in nitrogen and phosphorus fertilizers.

9. A method for synthetically and systemically improving nitrogen and phosphorus fertilizer use efficiency in a plant growth medium by purified homologous or heterologous endophytic bacteria producing protease enzymes, organic acids, alkaline phosphatase enzyme, and acid phosphatase enzyme sufficient to satisfy crop needs for optimal yields in said plant growth medium by colonizing the plant root and shoot at sufficient inoculum density that consists essentially of the following steps: 1) growing an endophytic bacteria having the ability to produce acid protease enzyme, alkaline protease, organic acids, alkaline phosphatase enzyme to inoculum density of $10^8$ to $10^{10}$ cfu/ml; 2) suspending the said inoculum in sterile phosphate buffer saline medium to a concentration of $10^8$ cfu/ml thereby providing an endophytic inoculum; 3) preparing the corn, sorghum, wheat, rice, and other vegetable, fruit, flower or grass seeds or plant parts by surface sterilizing with 95% ethanol for 2 min and 2.5% sodium hypochlorite for 20-30 min followed by washing seven times in sterile water; 4) soaking the aforementioned surface sterile seeds or plant parts in the said endophytic inoculum of step 2; 5) henceforth placing in a temperature controlled incubator at 25 degree C. for exactly 30 minutes with or without gentle shaking at 40-80 rpm, then washing the thus prepared inoculated seeds or plant part with 70% alcohol for 2 minutes and with 2% sodium hypochlorite followed by washing with sterile water 5 times; 6) treating the said prepared seeds or plant parts of step 5 with other seed treatments and coatings; 7) drying the said seed of step 6 before planting; and 8) planting the said prepared seeds or the said plant part in a plant growth medium with less than the recommended nitrogen and phosphorus fertilizer amount wherein the nitrogen is applied as urea, anhydrous ammonia, urea ammonium nitrate, ammonium nitrate, manure based fertilizers, composted fertilizers, high N- bat guano, single cell based proteins or another form and phosphorus is applied as is applied as triple superphosphate, diammonium phosphate, rock phosphate, manure or another form.

10. The method of claim 9 wherein in step 1, two or a plurality of endophytic bacteria are grown that each have optimal ability to produce acid proteas and alkaline protease enzymes and optimal ability to produce organic acids, acid phosphatase enzyme and alkaline phosphatase enzymes.

11. The method of claim 9, wherein the inoculated plant, plant part or seed is introduced in a plant growth medium in an amount effective to increase the yield of plants grown in said plant growth medium.

12. The method of claim 9 in which said endophytic inoculum, is introduced into a plant growth medium as part of an inoculant composition comprising at least $1\times10^5$ colony forming units of said endophytic inoculum per gram or per milliliter of inoculant composition.

13. The method of claim 9 in which said treated plant part comprises at least $1\times10^5$ colony forming units of said endophytic inoculum per kilogram of plant part.

14. The method of claim 9 in which said endophytic inoculum is introduced into a plant growth medium at a rate of at least $1\times10^5$ colony forming units of said endophytic inoculum per acre of plant growth medium.

15. The method of claim 9 wherein said endophytic inoculum is applied to plant seeds, one year before said plant seed is planted in a plant growth medium.

16. The method of claim 9 wherein a formulation containing said endophytic inoculum comprises at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient.

17. The method of claim 9 wherein said endophytic inoculum comprises the ability to induce in the agricultural plant production of protease enzymes, organic acids, and phosphatase enzymes.

18. The method of claim 9 wherein the endophytic bacteria is obtainable from interior or exterior of the agricultural plant.

19. The method of claim 9 wherein the endophytic bacteria is obtainable from a different cultivar, variety or crop as compared to the seed.

20. The method of claim 9 wherein the inoculation of endophytic bacteria in step 4 comprises spraying, immersing, coating, encapsulating, injecting or dusting the seeds with a formulation containing said endophytic inoculum and at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient.

* * * * *